(12) United States Patent
Yokoyama

(10) Patent No.: US 10,256,001 B2
(45) Date of Patent: Apr. 9, 2019

(54) METAL GRATING STRUCTURE FOR X-RAY

(71) Applicant: KONICA MINOLTA, INC., Chiyoda-Ku (JP)

(72) Inventor: Mitsuru Yokoyama, Chiyoda-ku (JP)

(73) Assignee: KONICA MINOLTA, INC., Tokyo (JP)

( * ) Notice: Subject to any disclaimer, the term of this patent is extended or adjusted under 35 U.S.C. 154(b) by 287 days.

(21) Appl. No.: 15/184,890

(22) Filed: Jun. 16, 2016

(65) Prior Publication Data

US 2016/0293284 A1    Oct. 6, 2016

Related U.S. Application Data

(62) Division of application No. 14/235,369, filed as application No. PCT/JP2012/004285 on Jul. 3, 2012.

(30) Foreign Application Priority Data

Jul. 27, 2011 (JP) .................. 2011-164015

(51) Int. Cl.
*G21K 1/06* (2006.01)
*G01N 23/20008* (2018.01)
*C25D 5/02* (2006.01)
*C25D 7/12* (2006.01)
*C25D 11/32* (2006.01)
*C25D 5/34* (2006.01)
(Continued)

(52) U.S. Cl.
CPC .............. *G21K 1/06* (2013.01); *C25D 5/022* (2013.01); *C25D 5/34* (2013.01); *C25D 7/12* (2013.01); *C25D 11/32* (2013.01); *G01N 23/20008* (2013.01); *G01N 23/20075* (2013.01); *G21K 1/025* (2013.01); *A61B 6/4035* (2013.01); *A61B 6/4291* (2013.01); *A61B 6/484* (2013.01); *G01N 2223/315* (2013.01); *G21K 2207/005* (2013.01)

(58) Field of Classification Search
CPC ..... A61B 6/4035; A61B 6/4291; A61B 6/484; G01N 23/20008; G01N 23/20075
See application file for complete search history.

(56) References Cited

U.S. PATENT DOCUMENTS

2011/0168908 A1    7/2011   Wang et al.
2013/0279651 A1   10/2013   Yokoyama

FOREIGN PATENT DOCUMENTS

JP    2007-239003    9/2007
JP    2009-037023    2/2009
(Continued)

OTHER PUBLICATIONS

J. Ohara et al., "A New Deep Reactive Ion Etching Process by Dual Sidewall Protection Layer", Denso Technical Review, vol. 5, No. 1, pp. 45-50, 2000.
(Continued)

*Primary Examiner* — Dani Fox
(74) *Attorney, Agent, or Firm* — Cozen O'Connor

(57) ABSTRACT

A metal grating structure for X-ray includes a first silicon part having a plate form or a layer form, and a grating portion, wherein the grating portion includes a plurality of second silicon parts formed on the first silicon part, and a plurality of metal parts interposed between the respective adjacent second silicon parts, each of the plurality of metal parts having a deposition start tip part extending toward an inside of the first silicon part.

12 Claims, 16 Drawing Sheets

(51) Int. Cl.
*G01N 23/20* (2018.01)
*G21K 1/02* (2006.01)
*A61B 6/00* (2006.01)

(56) References Cited

FOREIGN PATENT DOCUMENTS

| | | | | |
|---|---|---|---|---|
| JP | 2010-185728 | | 8/2010 | |
| JP | 2010185728 A | * | 8/2010 | ............... A61B 6/00 |
| JP | 2011-157622 | | 8/2011 | |

OTHER PUBLICATIONS

Office Action dated Jul. 19, 2016 which issued in the corresponding Japanese Patent Application No. 2013-525558.

* cited by examiner

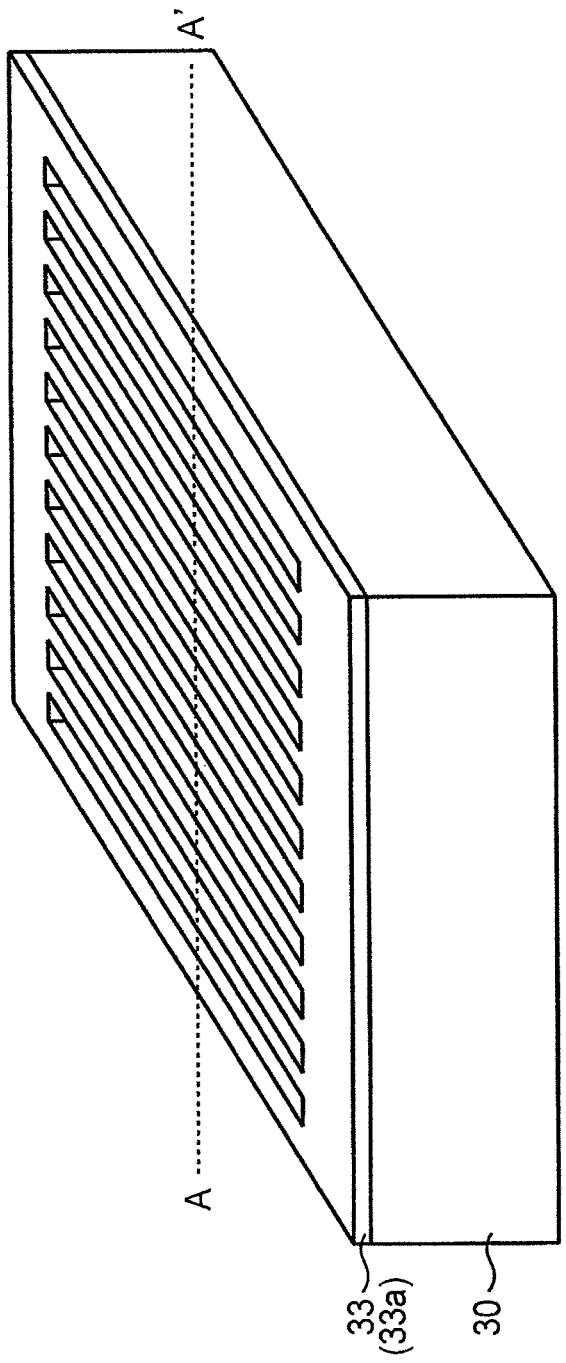

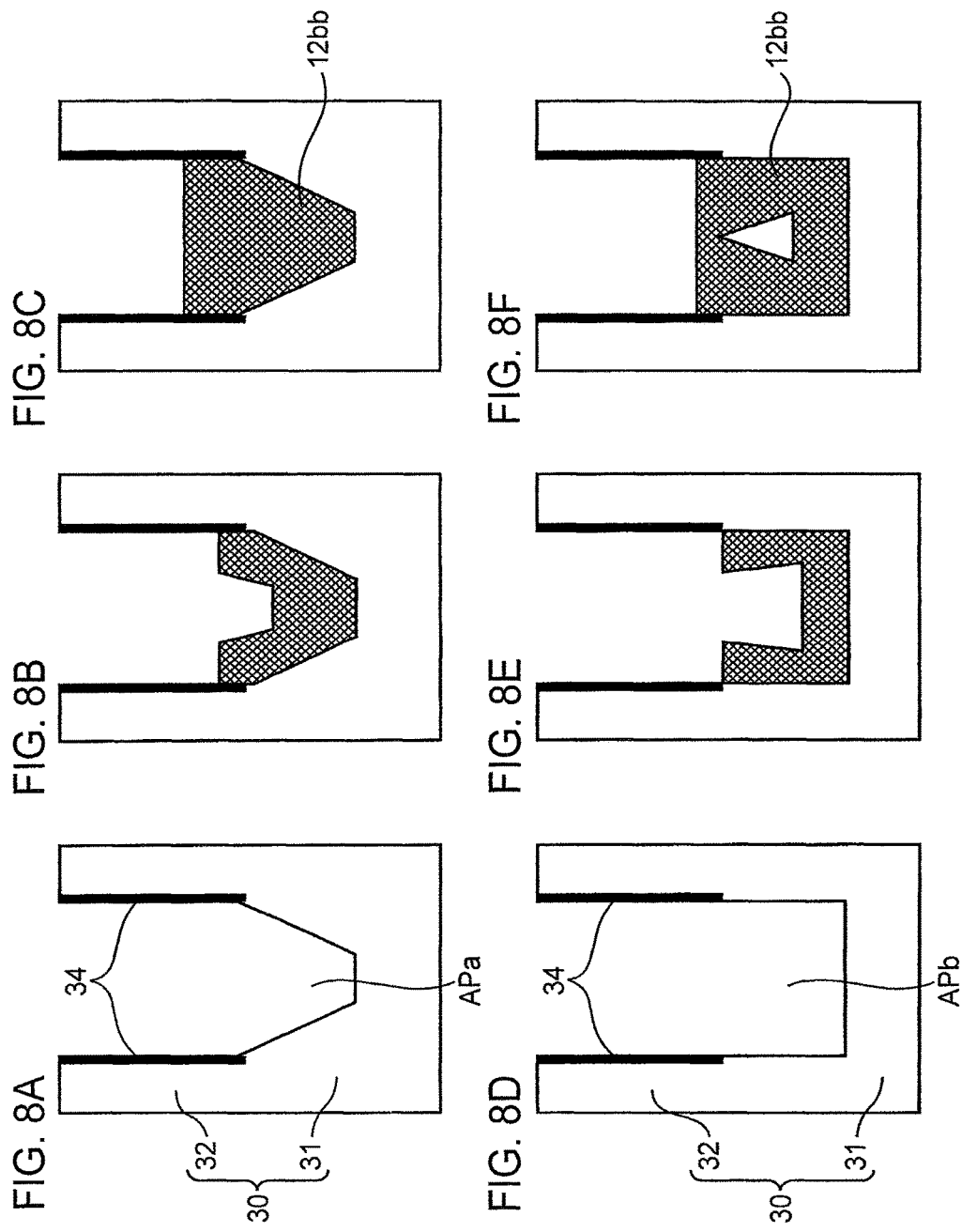

METAL GRATING STRUCTURE FOR X-RAY

RELATED APPLICATIONS

This application is a divisional of U.S. patent application Ser. No. 14/235,369 filed May 5, 2014 which is a U.S. National Phase Application under 35 USC 371 of International Application PCT/JP2012/004285 filed Jul. 3, 2012 which claims the priority of Japanese application No. 2011-164015 filed Jul. 27, 2011, the entire content of which is hereby incorporated by reference.

TECHNICAL FIELD

The present invention relates to a metal grating structure for X-ray suitably used for, for instance, a Talbot interferometer or a Talbot-Lau interferometer.

BACKGROUND ART

Diffraction gratings are utilized in optical systems of various devices, as a spectral element provided with multitudes of parallel periodic structures. In recent years, diffraction gratings are also applied to X-ray imaging devices. Diffraction gratings are roughly classified into transmissive diffraction gratings and reflective diffraction gratings according to diffraction methods. The transmissive diffraction gratings include amplitude-type diffraction gratings (absorptive diffraction gratings) in which light absorption parts are periodically arranged on a substrate for transmitting light, and phase-type diffraction gratings in which parts for shifting the phase of light are periodically arranged on a substrate for transmitting light. In the present specification, absorption means light of an amount larger than 50% of the total light amount is absorbed by a diffraction grating, and transmission means light of an amount larger than 50% of the total light amount is transmitted through a diffraction grating.

Diffraction gratings for near infrared light, visible light, or ultraviolet light can be relatively easily manufactured in view of a point that near infrared light, visible light, and ultraviolet light are sufficiently absorbed by a very thin metal film. For instance, forming a metal film on a substrate by metal vapor deposition on the substrate such as a glass plate, and forming the metal film into a grating pattern enables to manufacture an amplitude-type diffraction grating by a metal grating structure. In an amplitude-type diffraction grating for visible light, in the case where aluminum (Al) is used as metal, forming a metal film having a thickness of about 100 nm for instance is sufficient, because the transmittance of visible light (a wavelength in the range of from about 400 nm to about 800 nm) through aluminum is 0.001% or less.

On the other hand, as is well known, generally, X-ray has a property that absorption by matter is very low, and the phase shift is not so large. Even in the case where a diffraction grating for X-ray is manufactured with use of gold (Au), which is a preferable material, it is necessary to form a gold film of about 100 µm in thickness. In the case where periodic structures are formed, with light transmissive parts and light absorption parts/phase shifting parts of a same width and at a pitch of several µm to several ten µm, the ratio (an aspect ratio=thickness/width) of thickness to width of the gold part is as high as 5 or more. It is not easy to manufacture a structure having such a high aspect ratio. In view of the above, patent literature 1 is proposed as a method for manufacturing a diffraction grating provided with a structure of such a high aspect ratio.

The diffraction grating manufacturing method disclosed in patent literature 1 is a method for manufacturing a diffraction grating for use in an X-ray Talbot interferometer, and has the following steps. First of all, a metal sheet layer is formed on one surface of a glass substrate. Then, patterning is performed by coating an ultraviolet photosensitive resin on the metal sheet layer, and subjecting the ultraviolet photosensitive resin to pattern exposure with use of an optical lithography mask for a phase-type diffraction grating followed by development. Then, an X-ray absorbing metal part is formed on a portion of the metal sheet layer where the ultraviolet photosensitive resin is removed, by a metal plating method. Then, the patterned ultraviolet photosensitive resin, and a portion of the metal sheet layer corresponding to the patterned ultraviolet photosensitive resin are removed. By performing the above operation, a phase-type diffraction grating is manufactured. Then, patterning is performed by coating an ultraviolet photosensitive resin on a surface of the phase-type diffraction grating corresponding to the one surface of the glass substrate, and by subjecting the ultraviolet photosensitive resin to pattern exposure from the other surface of the phase-type diffraction grating with use of the phase-type diffraction grating as an optical lithography mask followed by development. Then, applying a voltage via the metal sheet layer by a metal plating method forms an X-ray absorbing metal part on the X-ray absorption part of the phase-type diffraction grating, on a portion where the ultraviolet photosensitive resin is removed. Thereafter, the aforementioned steps are repeated until the X-ray absorbing metal part has a required thickness, with use of a phase-type diffraction grating having the newly formed X-ray absorbing metal part, as a new optical lithography mask. Thus, an amplitude-type diffraction grating is manufactured.

In the diffracting grating manufacturing method disclosed in patent literature 1, the aforementioned steps are repeated until the X-ray absorbing metal part has a required thickness. This requires a certain time and involves a cumbersome operation.

In view of the above, there is proposed an idea of manufacturing a diffraction grating by a metal grating structure by utilizing the properties of a silicon substrate capable of forming a three-dimensional structure of a high aspect ratio. Specifically, there is proposed a method for manufacturing a diffraction grating by forming slit grooves having periodic structures of a high aspect ratio in a silicon substrate, and by filling metal in the slit grooves by an electroplating method (an electroforming method) utilizing conductivity of a silicon substrate.

In the above method, however, since the entirety of a silicon substrate has conductivity, the metal is deposited not only on the bottom of the slit groove but also on the side surfaces of the slit groove. As a result, space (a void or a portion where metal is not filled) may be formed in the metal part. Thus, it is difficult to finely fill the slit groove with the metal by an electroforming method.

CITATION LIST

Patent Literature

Patent literature 1: JP 2009-037023A

SUMMARY OF INVENTION

In view of the above, an object of the present invention is to provide a metal grating structure for X-ray that enables to finely form metal parts of a grating structure by an electroforming method, with use of a silicon substrate.

The metal grating structure for X-ray of the present invention includes a first silicon part having a plate form or a layer form, and a grating portion, wherein the grating portion includes a plurality of second silicon parts formed on the first silicon part, and a plurality of metal parts interposed between the respective adjacent second silicon parts, each of the plurality of metal parts having a deposition start tip part extending toward an inside of the first silicon part.

These and other objects, features and advantages of the present invention will become more apparent upon reading the following detailed description along with the accompanying drawings.

BRIEF DESCRIPTION OF DRAWINGS

FIG. 5 is a perspective view showing a silicon substrate during a step of the metal grating structure manufacturing method according to the embodiment;

FIGS. 8A through 8F are diagrams for describing a difference in metal deposition in an electroforming step due to a difference in sectional shape of a bottom part of a concave part;

DESCRIPTION OF EMBODIMENTS

Figure 1:
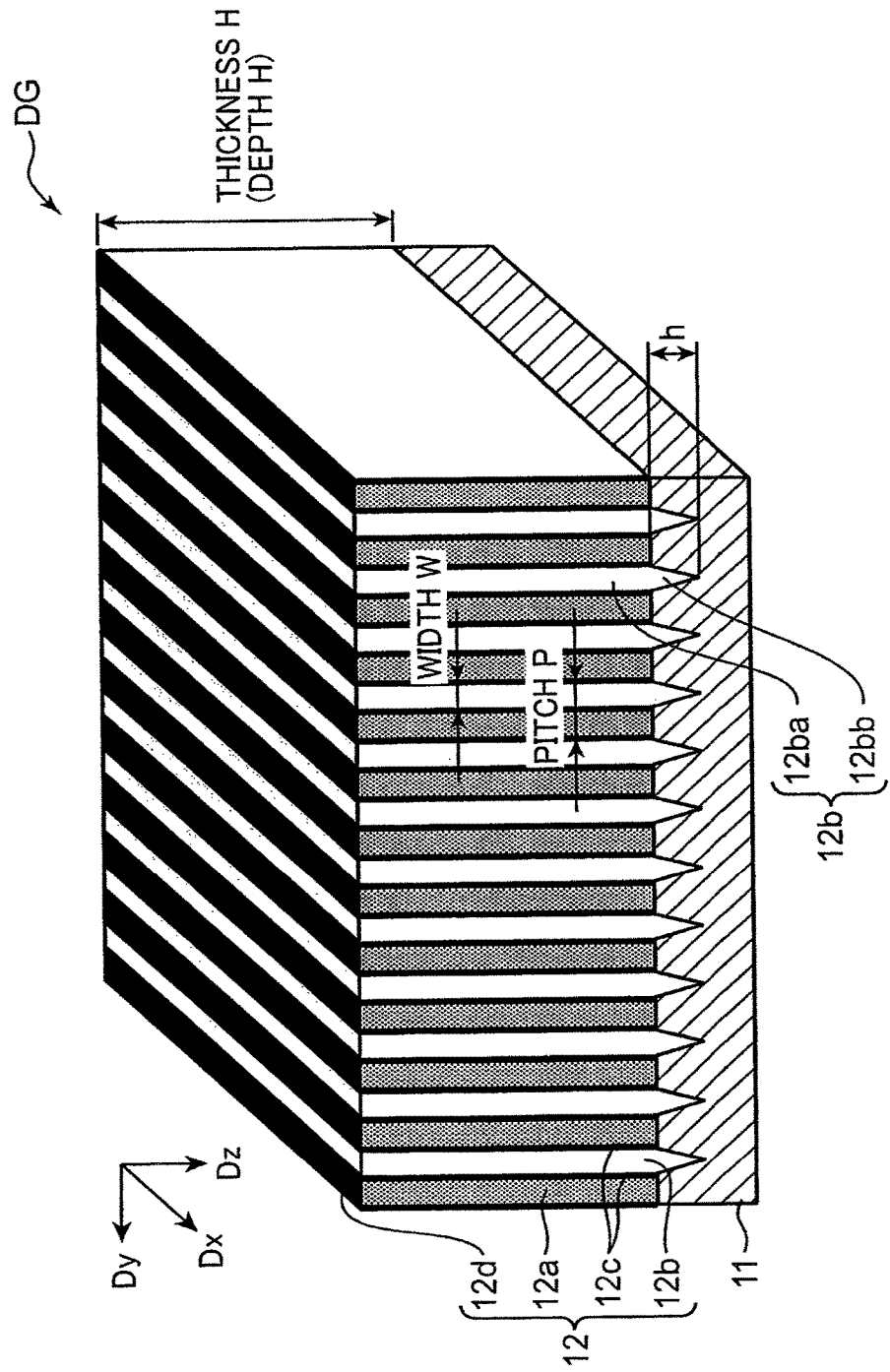
FIG. 1 is a perspective view showing a configuration of a metal grating structure according to an embodiment.

In the following, an embodiment of the present invention is described referring to the accompanying drawings. Constructions identified by the same reference numerals in the drawings are the same constructions and not repeatedly described unless necessary. Further, in the specification, in the case where the elements are generically referred to, the elements are indicated with reference numerals without suffixes, and in the case where the elements are individually referred to, the elements are indicated with reference numerals with suffixes.

(Metal Grating Structure)

FIG. 1 is a perspective view showing a configuration of a metal grating structure according to an embodiment. As shown in FIG. 1, a metal grating structure DG according to the embodiment is provided with a first silicon part 11, and a grating portion 12 formed on the first silicon part 11. As shown in FIG. 1, the first silicon part 11 has a plate form or a layer form extending along the DxDy plane, in the case where a DxDyDz orthogonal coordinate system is defined. The grating portion 12 has a predetermined thickness H (a length in the Dz direction perpendicular to the grating plane DxDy (a direction normal to the grating plane DxDy)). The grating portion 12 includes plural second silicon parts 12a, each of which linearly extends in one direction Dx, and plural metal parts 12b, each of which has the predetermined thickness H and linearly extends in the one direction Dx. The second silicon parts 12a and the metal parts 12b are alternately disposed in parallel to each other. Accordingly, the metal parts 12b are disposed away from each other at a predetermined interval in a direction Dy orthogonal to the one direction Dx. In other words, the second silicon layers 12a are disposed away from each other at a predetermined interval in the direction Dy orthogonal to the one direction Dx. The predetermined interval (pitch) P is made constant in the embodiment. Specifically, the metal parts 12b (the second silicon parts 12a) are disposed at the same interval P in the direction Dy orthogonal to the one direction Dx. Each of the second silicon parts 12a has a plate form or a layer form extending along the DxDz plane orthogonal to the DxDy plane. Each of the metal parts 12b has a grating part 12ba having a plate form or a layer form extending along the DxDz plane and interposed between the respective adjacent second silicon parts 12a, and a deposition start tip part 12bb extending from one end of the grating part 12ba toward the inside of the first silicon part 11.

Further, plural first insulating layers 12c are formed between the respective second silicon parts 12a and the respective grating parts 12ba of the metal parts 12b. Specifically, a first insulating layer 12c is formed on both side surfaces of each of the second silicon parts 12a. In other words, the first insulating layer 12c is formed on both side surfaces of each of the grating parts 12ba of the metal parts 12b. The first insulating layer 12c has a function of electrically insulating between the second silicon part 12a and the grating part 12ba of the metal part 12b, and is formed of an oxide film, for instance. Examples of the oxide film is a silicon oxide film (an $SiO_2$ film or an oxidized silicon film) and an alumina film (an $Al_2O_3$ film or an aluminum oxide film). On the other hand, the aforementioned insulating layer is not formed between the respective second silicon parts 12a and the respective deposition start tip parts 12bb of the metal parts 12b. The second silicon parts 12a and the deposition start tip parts 12bb of the metal parts 12b are electrically conductive to each other.

Further, second insulating layers 12d are formed on upper surfaces (apex parts) of the respective second silicon parts 12a. The second insulating layer 12d functions as an element for electrically insulating the second silicon part 12a by an electroforming method described later. The second insulating layer 12d is made of a photosensitive resin layer (a photoresist film) or an oxide film, for instance. Examples of the oxide film are a silicon oxide film and an alumina film.

The first silicon part 11, the second silicon parts 12a, the first insulating layers 12c, and the second insulating layers 12d function to transmit X-ray, and the metal parts 12b function to absorb X-ray. In particular, the grating parts 12ba of the metal parts 12b mainly function to absorb X-ray. Accordingly, the metal grating structure DG according to one aspect functions as a diffraction grating by appropriately setting the predetermined interval P according to the wavelength of X-ray. Metal composing the metal part 12b is preferentially selected from the metals absorbing X-ray. Examples of the metal include metal elements or precious metal elements having a relatively heavy atomic weight, specifically, gold (Au), platinum (Pt), rhodium (Rh), ruthenium (Ru), and iridium (Ir). Further, the grating part 12ba of the metal part 12b has an appropriate thickness H so as to sufficiently absorb X-ray according to the device specifications, for instance. In view of the above, the ratio (an aspect ratio=thickness/width) of thickness H to width W of the grating part 12ba of the metal part 12b is set to an aspect ratio as high as 5 or more. The width W of the grating part 12ba of the metal part 12b corresponds to the length of the grating part 12ba of the metal part 12b in the direction (a width direction) Dy orthogonal to the one direction (a longitudinal direction) Dx, and the thickness H of the grating part 12ba of the metal part 12b corresponds to the length of the grating part 12ba of the metal part 12b in the direction (a depth direction) Dz normal to the plane DxDy defined by the one direction Dx and the direction Dy orthogonal to the one direction Dx.

The metal grating structure DG provided with the metal parts 12b having such a high aspect ratio is manufactured by a resist layer forming step of forming a resist layer on a principal plane of a silicon substrate; a patterning step of patterning the resist layer, and removing the patterned portion of the resist layer; an etching step of etching the silicon substrate at a portion where the resist layer is removed by a dry etching method, and forming a concave part of a predetermined depth; an insulating layer forming step of forming an insulating layer on an inner surface of the concave part in the silicon substrate; a removing/surface area increasing step of removing a portion of the insulating layer formed on a bottom part of the concave part, and etching the silicon substrate at the bottom part of the concave part to increase the surface area of the bottom part of the concave part; and an electroforming step of applying a voltage to the silicon substrate to fill the concave part with metal by an electroforming method. For instance, the concave part is a slit groove in the case of a one-dimensional grating structure, and is a columnar hole (a columnar pore) in the case of a two-dimensional grating structure. In the following, a method for manufacturing the metal grating structure DG in which the concave part is a slit groove is described in detail. The same description is applied to a configuration, in which a concave part has another shape such as a columnar hole.

(First Manufacturing Method)

FIGS. 2A through 4C are diagrams for describing a first metal grating structure manufacturing method according to an embodiment. FIG. 5 is a perspective view showing a silicon substrate during a step of the metal grating structure manufacturing method according to the embodiment.

Figure 2A:
FIGS. 2A through 2C are diagrams (part 1) for describing a first metal grating structure manufacturing method according to an embodiment.

In order to manufacture the metal grating structure DG according to the embodiment, at first, a silicon substrate 30 is prepared (see FIG. 2A). Preferably, the silicon substrate 30 is an n-type silicon substrate, in which most of the carriers are electrons.

The n-type silicon substrate is rich in conductive electrons. Accordingly, connecting the silicon substrate to the negative pole of a power source and applying a negative potential to the silicon substrate for obtaining cathode polarization causes a so-called ohmic contact with a plating solution 46 in an electroforming step described later. This allows a current to flow and makes it easy to cause a reduction reaction. This makes it easy to precipitate metal.

Figure 2B:
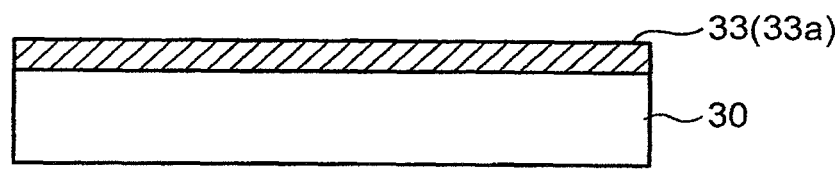
Figure 2C:
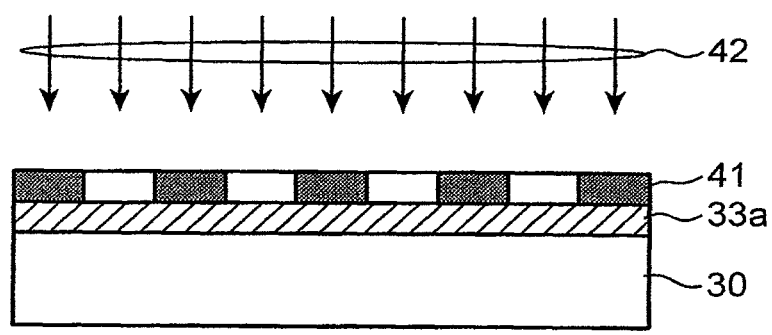

Then, a resist layer 33 is formed on the principal plane of the silicon substrate 30 (a resist layer forming step, see FIG. 2B). The resist layer 33 is patterned, and the patterned portion of the resist layer 33 is removed (a patterning step, see FIG. 2C and FIG. 3A). The resist layer is a layer which functions as a protective film against etching in performing the etching.

For instance, the resist layer 33 may be made of a material having resistance in an etching process in an etching step that follows next. The term "having resistance" does not necessarily mean that a target portion is not etched at all, but a target portion is less likely to be etched in an etching process. This means that during etching of a portion to be etched, the resist layer acts as a protective film which protects a portion that should not be etched. The resist layer 33 is formed to have a film thickness that remains after an etching step that follows next, and after a removing/surface area increasing step described later. In the embodiment, a photosensitive resin layer (a photoresist layer) 33a is used as the resist layer 33.

More specifically, the photosensitive resin layer 33a is formed on the silicon substrate 30 by spin coating, for instance (see FIG. 2B). The photosensitive resin layer 33a is formed to have a predetermined film thickness of about 2 µm, and functions as a protective film that protects a plate like part 32 (a wall part 32, the second silicon part 12a, see FIG. 4A) of the silicon substrate 30 against an etching process in the etching step (see FIG. 3B) and a removing process in the removing/surface area increasing step (see FIG. 4A and FIG. 4B) described later. In this example, the photosensitive resin layer 33a is made of a material used in lithography, and having a physical property such that the solubility thereof changes by light (not only including visible light but also including ultraviolet light) or an electron beam. The present embodiment is not limited to the above. For instance, a resist layer 33a for electron beam exposure may be formed, in place of the photosensitive resin layer 33a. Subsequently, as a photolithography step, the photosensitive resin layer 33a is patterned by a lithography method (see FIG. 2C), and the patterned portion of the photosensitive resin layer 33a is removed (see FIG. 3A). More specifically, a lithography mask 41 is pressed against the photosensitive resin layer 33a, ultraviolet light 42 is irradiated onto the photosensitive resin layer 33a via the lithography mask 41, and the photosensitive resin layer 33a is subjected to pattern exposure followed by development (see FIG. 2C). Then, the unexposed portion (or the exposed portion) of the photosensitive resin layer 33a is removed (see FIG. 3A).

Figure 3A:
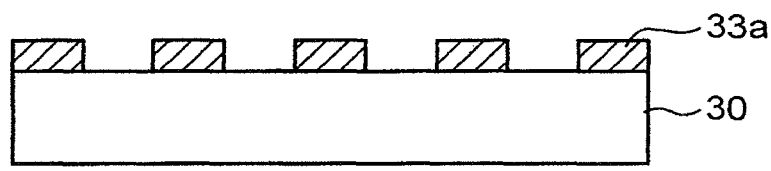
FIGS. 3A through 3C are diagrams (part 2) for describing the first metal grating structure manufacturing method according to the embodiment.
Figure 3B:
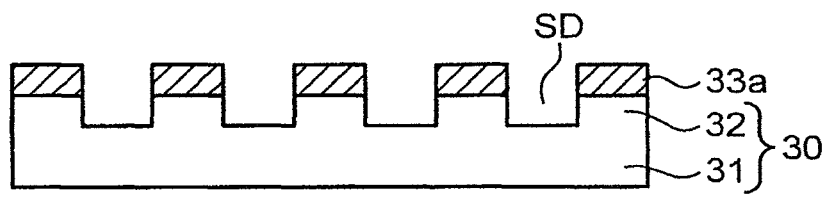

Subsequently, a portion of the silicon substrate 30 where the photosensitive resin layer 33 is removed is etched to a first predetermined depth H in the normal direction Dz by a dry etching method. By the above process, a slit groove SD is formed (see FIG. 3B, an etching step). More specifically, the silicon substrate 30 is etched to the first predetermined depth H from the surface of the silicon substrate 30 by ICP dry etching, with use of the patterned photosensitive resin layer 33a as a mask. By the ICP dry etching, the photosensitive resin layer 33a is removed to some extent. However, the photosensitive resin layer 33a of a predetermined film thickness remains, and functions as a protective film that protects the plate like part 32 (the second silicon part 12a) of the silicon substrate 30 in the removing/surface area increasing step (see FIG. 4B) described later. In the foregoing example, the photosensitive resin layer 33a is reduced from a thickness of about 2 μm to a thickness of about 1 μm, and the photosensitive resin layer 33a of about 1 μm in thickness remains. FIG. 5 shows a structure example of the silicon substrate 30 which has undergone the etching step. FIG. 3B shows a cross section of the silicon substrate 30 taken along the line A-A' in FIG. 5.

The ICP dry etching makes it possible to perform vertical etching with a high aspect ratio. Accordingly, the ICP dry etching is preferably an ASE process by an ICP apparatus. The ASE (Advanced Silicon Etch) process is a process including a step of etching a silicon substrate by RIE (reactive ion etching) with use of F radicals and F ions in $SF_6$ plasma, and a step of depositing a polymer film having a composition analogous to Teflon (registered trademark) on a wall surface by polymerization reaction of $CF_X$ radicals and ions thereof in $C_4F_8$ plasma for functioning the polymer film as a protective film, wherein the above steps are repeatedly performed. Further, ICP dry etching is advantageous in performing vertical etching with a high aspect ratio. Accordingly, it is more preferable to alternately perform side wall protection and bottom surface etching by alternately repeating a state enriched with $SF_6$ plasma and a state enriched with $C_4F_8$ plasma, like a Bosch process. The dry etching method is not limited to the ICP dry etching, but any other technique may be applied. For instance, an etching technology such as parallel plate type reactive ion etching (RIE), dry etching with magnetic neutral line plasma (NLD), chemically assisted ion beam (CAIB) etching, or electron cyclotron resonance reactive ion beam (ECRIB) etching may be applied.

A plate like part (a layer like part or a wall part) 32 of the silicon substrate 30 that remains along the DxDz plane after the etching serves as a second silicon part 12a, and a plate like part (a base part) 31 of the silicon substrate 30 that remains along the DxDy plane after the etching serves as a first silicon part 11.

Figure 3C:
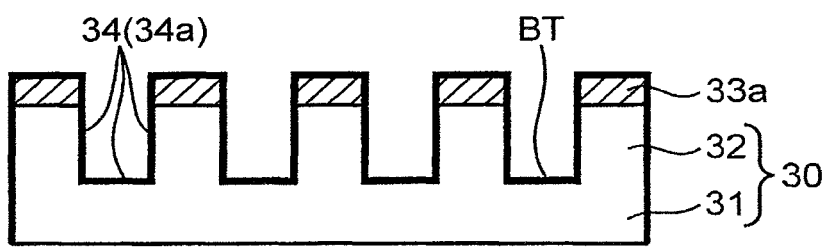

Subsequently, an insulating layer 34 of a predetermined thickness is formed over the entirety of the principal plane surface of the silicon substrate 30 where the slit grooves SD are formed by an anodic oxidation method to have an insulating property in an electroforming method in an electroforming step described later (see FIG. 3C, an insulating layer forming step). In this example, the insulating layer 34 is a silicon oxide film 34a because the silicon substrate 30 is used. In the anodic oxidation method, the silicon substrate 30 is connected to the positive pole of a power source, and a cathode electrode connected to the negative pole of the power source and the silicon substrate 30 are immersed in an electrolytic solution. When a current is supplied to the silicon substrate 30 in this state, a silicon oxide film 34a of a predetermined thickness (e.g. about 20 nm) is formed on the surface of the silicon substrate 30. Preferably, the electrolytic solution may be an acidic solution which has strong oxidation power but does not dissolve an oxide film formed by anodic oxidation. Examples of the electrolytic solution are aqueous solutions of nitric acid, hydrochloric acid, sulfuric acid, oxalic acid, and phosphoric acid. Preferably, the cathode electrode may be formed of metal that is not dissolved in the electrolytic solution, such as gold (Au) or platinum (Pt).

Subsequently, a portion of the insulating layer 34 formed on the bottom part BT of the slit groove SD is removed, and the base part 31 of the silicon substrate 30 at the bottom part BT of the slit groove SD is etched to a second predetermined depth h to increase the surface area of the bottom part of the slit groove SD as compared with a state before the etching (see FIG. 4A and FIG. 4B, a removing/surface area increasing step). Specifically, a portion of the insulating layer 34 formed on the bottom part BT of the slit groove SD is removed (see FIG. 4A, a removing step). Subsequently, the base part 31 of the silicon substrate 30 at the bottom part BT of the slit groove SD is etched to the second predetermined depth h (see FIG. 4B, a surface area increasing step). By the surface area increasing step, the surface area of the bottom part of the slit groove SD is increased, as compared with a state before the etching.

Figure 4A:
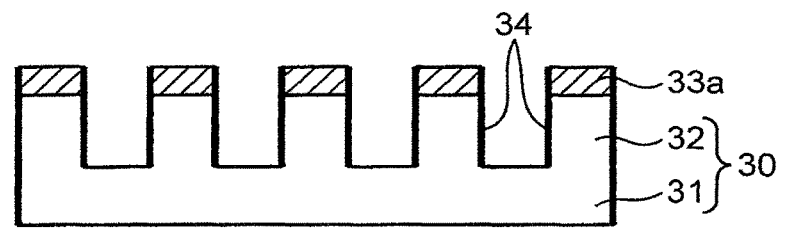
FIGS. 4A through 4C are diagrams (part 3) for describing the first metal grating structure manufacturing method according to the embodiment.

More specifically, in the removing step, a portion of the insulating layer 34 formed on the bottom part BT of the slit groove SD by ICP dry etching with use of $CHF_3$ gas is etched and removed (see FIG. 4A).

In this example, the photosensitive resin layer 33a is also etched by the ICP dry etching. However, the photosensitive resin layer 33a of a sufficient thickness remains after the removing step. Accordingly, the photosensitive resin layer 33a of a certain thickness remains after the ICP dry etching. In the foregoing example, the photosensitive resin layer 33a which has undergone the ICP drying etching has a thickness of from 1 μm to 700 nm.

Figure 4B:
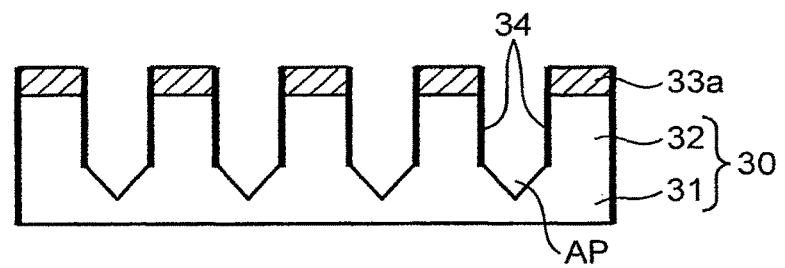
Figure 6:
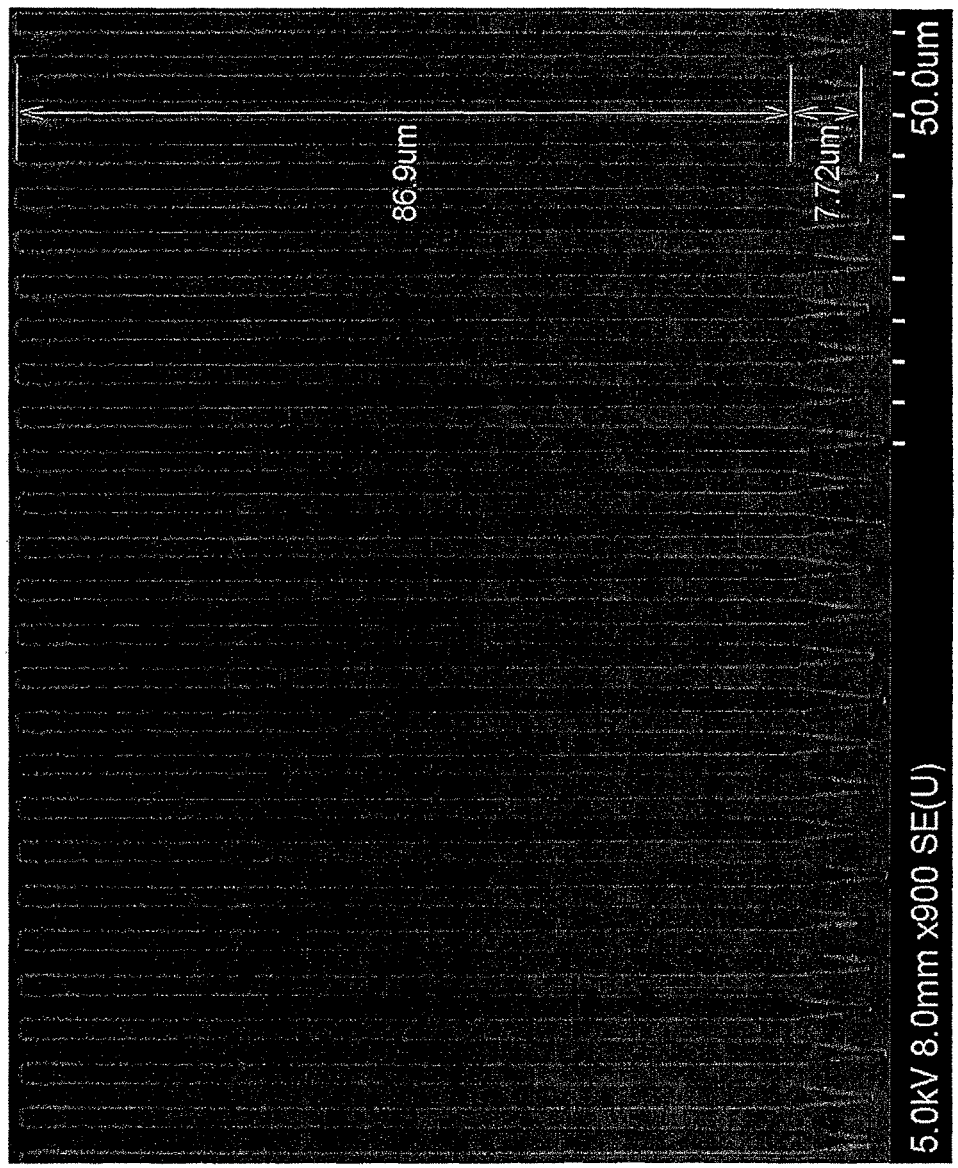
FIG. 6 is a diagram showing a state of a silicon substrate which has undergone a removing/surface area increasing step.

In the surface area increasing step, gas suitable for etching a silicon substrate is used, and the base part 31 of the silicon substrate 30 at the bottom part BT of the slit groove SD is etched to the second predetermined depth h by ICP dry etching (see FIG. 4B). For instance, ICP dry etching of alternately repeating a state enriched with $SF_6$ plasma and a state enriched with $C_4F_8$ plasma is performed like a Bosch process. In this example, by setting a time for making $C_4F_8$ plasma enriched state (a deposition state) longer than a time for making a $SF_6$ plasma enriched state (an etching state), the side wall protection may be excessively performed. As shown in FIG. 4B and FIG. 6, side surfaces of a deposition start tip concave part AP, which is newly formed by etching the plate like part 31 of the silicon substrate 30 at the bottom part BT of the slit groove SD, have a tapered shape. By the aforementioned surface area increasing step, for instance, the base part 31 of the silicon substrate 30 is etched by 7,700 nm FIG. 6 is an electron micrograph showing an example of a state of the silicon substrate 30 which has undergone the removing/surface area increasing step. In the example shown in FIG. 6, the depth of the slit groove SD formed by the etching step is 86.9 μm, and the depth of the deposition start tip concave part AP formed by the removing/surface area increasing step is 7.72 μm.

Further, the ICP dry etching has high vertical directionality. Accordingly, the insulating layer 34 formed on the inner side surfaces of the slit groove SD (the insulating layer 34 formed on both wall surfaces (both side surfaces) of the wall part 32 of the silicon substrate 30) has a sufficient thickness capable of functioning as an insulating layer at the point of time when the portion of the insulating layer 34 formed on the bottom part BT of the slit groove SD is removed. The insulating layer 34 formed on the inner side surfaces of the slit groove SD may have such a thickness as to exhibit a function of cutting off a voltage to be applied to the plate like part 32 of the silicon substrate 30 (a function of electrically insulating the wall part 32) in the electroforming step that follows next, for instance, may have a thickness of about 10 nm or more by cooperation with the resist layer 33 (the photosensitive resin layer 33a) having an insulating property. The insulating layers 34 formed on the inner side surfaces of the slit grooves SD (the insulating layers 34 formed on both wall surfaces (both side surfaces) of the wall parts 32 of the silicon substrate 30) serve as first insulating layers 12c formed between the respective second silicon parts 12a and the respective metal parts 12b.

In the foregoing example, different gases are used between the removing step and the surface area increasing step in order to use gas suitable for an object to be etched. In the case, however, where the thickness of the insulating layer 34 formed on the bottom part BT of the slit groove SD is relatively small, it is also possible to use, in the removing step, the gas suitable for etching a silicon substrate in the surface area increasing step. It is possible to gradually remove the insulating layer 34 by kinetic energy of the gas suitable for etching a silicon substrate by collision of ionized molecules with the insulating layer 34, regardless of use of the gas suitable for etching a silicon substrate. Conversely, it is also possible to use, in the surface area increasing step, the gas used in the removing step for gradually etching a silicon substrate. In this way, using a same gas in the removing step and in the surface area increasing step eliminates the need of changing gases between the steps. This is advantageous in simplifying the steps.

The silicon substrate 30 which has undergone the resist layer forming step, the patterning step, the etching step, the insulating layer forming step, and the removing/surface area increasing step in this order is an intermediate product for a metal grating structure. The intermediate product for a metal grating structure is constituted of a silicon substrate 30 having plural slit grooves SD according to a predetermined pattern, wherein each of the slit grooves SD has an insulating layer 34 formed on the inner surface of the slit groove SD from an opening end to a position corresponding to the first predetermined depth H in a depth direction, and the silicon substrate 30 is exposed from the inner surface in a region from the position corresponding to the first predetermined depth H to the deepest end of the slit groove SD.

Figure 4C:
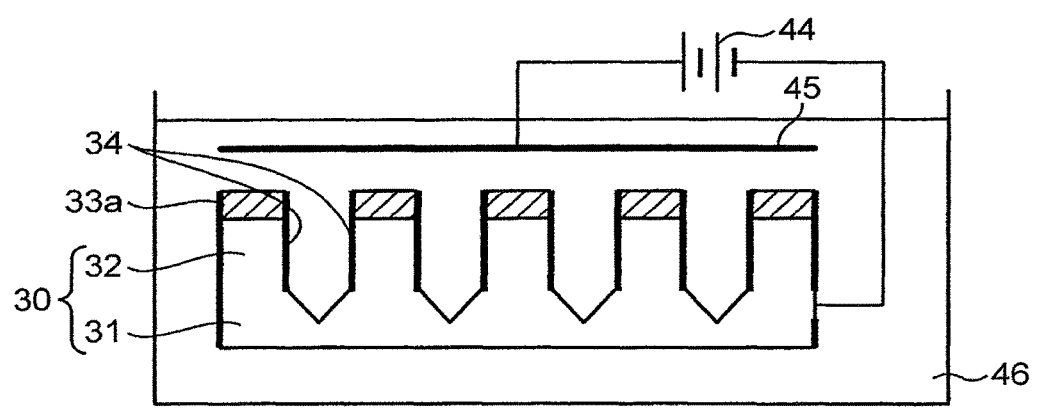

Subsequently, the slit groove SD is filled with metal by applying a voltage to the silicon substrate 30 by an electroforming method (an electroplating method) (an electroforming step, see FIG. 4C). More specifically, the negative pole of a power source 44 is connected to the silicon substrate 30, and an anode electrode 45 connected to the positive pole of the power source 44 and the silicon substrate 30 are immersed in a plating solution 46. In order to securely penetrate the plating solution 46 into the slit grooves SD of a high aspect ratio, various treatments may be performed. For instance, the surface of an intermediate product for a metal grating structure, as an object to be plated, may be made hydrophilic by alkali treatment; ultrasonic vibration may be applied to the intermediate product for a metal grating structure in a state that the intermediate product is immersed in the plating solution 46; the intermediate product for a metal grating structure in the plating solution 46 may be put in a vacuum chamber for drawing the air from the inside of the slit grooves SD, followed by immersion into the plating solution 46 in the above state; or the intermediate product for a metal grating structure immersed in the plating solution 46 may be vacuum-degassed for drawing the air from the inside of the slit grooves SD. In the case where a silicon oxide film is formed on a portion of the silicon substrate 30 to be connected to the negative pole of the power source 44, the portion of the silicon oxide film is removed for electric conduction between the negative pole of the power source 44 and the silicon substrate 30. By performing the above treatment, metal is precipitated and deposited on the silicon substrate 30 (the base part 31) side at the deposition start tip concave part AP communicating with the slit groove SD by electroforming. Then, when the metal fills the deposition start tip concave part AP and the slit groove SD, the electroforming is ended. By performing the above treatment, the metal fills the deposition start tip concave part AP, and is deposited by the same thickness H as the plate like part 32 of the silicon substrate 30. In this way, metal fills the deposition start tip concave part AP and the slit groove SD, and the deposition start tip part 12bb and the grating part 12ba of the metal part 12b are formed. The metal is preferentially selected from the elements capable of absorbing X ray, for instance, metal elements or precious metal elements having a relatively heavy atomic weight, specifically, gold (Au), platinum (Pt), rhodium (Rh), ruthenium (Ru), iridium (Ir), indium (In), and nickel (Ni).

The metal grating structure DG having the configuration as shown in FIG. 1 is manufactured by performing the above manufacturing steps.

In the method for manufacturing a metal grating structure DG having the above configuration, the silicon substrate 30 is dry etched. Accordingly, it is possible to form a slit groove SD of a high ratio of depth H to width W of the slit groove SD (an aspect ratio of the slit groove SD=depth H/width W). Thus, the metal grating structure DG manufacturing method having the above configuration is capable of manufacturing a metal grating structure DG provided with a grating part 12ba of a metal part 12b having a high aspect ratio by filling a slit groove SD having a high aspect ratio with metal. Then, in filling the slit groove SD with metal by an electroforming method in the electroforming step, at first, an insulating layer 34 is formed on the inner surface of the slit groove SD in the insulating layer forming step, specifically, in the embodiment, a silicon oxide film (an SiO$_2$ film) is formed on the inner surface of the slit groove SD by an anodic oxidation method. Subsequently, in the removing step of the removing/surface area increasing step, a portion of the insulating layer 34 formed on a bottom part BT of the slit groove SD is removed. Further, in the surface area increasing step of the removing/surface area increasing step, a plate like part 31 of the silicon substrate 30 exposed from the bottom part of the slit groove SD is etched to form a deposition start tip concave part AP having the second depth h, whereby the surface area of the bottom part of the slit groove SD is increased, as compared with a state before the etching (before the surface area increasing step is performed). Accordingly, in the insulating layer forming step, it is possible to form a silicon oxide film 34a of a predetermined film thickness, and to insulate, by the silicon oxide film 34a, a wall surface portion (a wall surface portion (inner side surface portions) of the slit groove SD) of a wall part 32 of the silicon substrate 30 (each of the plate like parts 32 of the silicon substrate 30) that constitutes the slit groove SD and remains in the etching step, while making the bottom part of the slit groove SD electrically conductive. Accordingly, metal is securely precipitated and deposited on the bottom part of the slit groove SD, without precipitating and depositing the metal on the wall surface (inner side surfaces) of the slit groove SD. Thus, the metal grating structure DG manufacturing method having the above configuration can effectively prevent formation of voids, because the metal is preferentially deposited on the bottom part of the slit groove SD. Accordingly, the metal grating structure DG manufacturing method having the above configuration is advantageous in finely forming the metal parts 12b of a grating structure by an electroforming method. In particular, a diffraction grating to be used in an X-ray Talbot interferometer and an X-ray Talbot-Lau interferometer requires a high aspect ratio in a grating part 12ba of a metal part 12b. The metal grating structure DG manufacturing method according to this embodiment can secure such a high aspect ratio, for instance, an aspect ratio of 5 or more, preferably 10 or more, and more preferably 20 or more. In addition, the above method makes it possible to form a fine grating part 12ba of a metal part 12b. Thus, the above method is suitable as a method for manufacturing a diffraction grating for use in an X-ray Talbot interferometer and an X-ray Talbot-Lau interferometer.

Further, according to the embodiment, in the removing/surface area increasing step, in addition to removing the insulating layer 34 formed on the bottom part BT of the slit groove SD in the removing step, the base part 31 of the silicon substrate 30 exposed from the bottom part BT of the slit groove SD is etched to the second predetermined depth h in the surface area increasing step to increase the surface area of the bottom part BT of the slit groove SD, as compared with a state before the etching (before the surface area increasing step is performed). In the above configuration, the surface area of the silicon substrate 30 to be exposed increases. As a result, the electrically conductive surface area in the electroforming step increases. This is advantageous in suppressing a variation of metal deposition speed in each of the slit grooves SD. Thus, the metal grating structure DG manufacturing method according to the embodiment is advantageous in manufacturing a metal grating structure DG having a substantially uniform deposition length of a metal part in each of the slit grooves SD by an electroforming method.

Figure 7A:
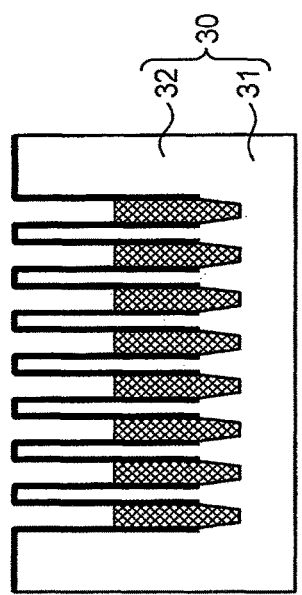
FIGS. 7A through 7D are diagrams for describing a difference in metal deposition in the case where an electroforming step is performed after a removing/surface area increasing step, and in the case where an electroforming step is performed after a removing step of removing only an insulating layer formed on bottom parts of concave parts.
Figure 7B:
Figure 7D:
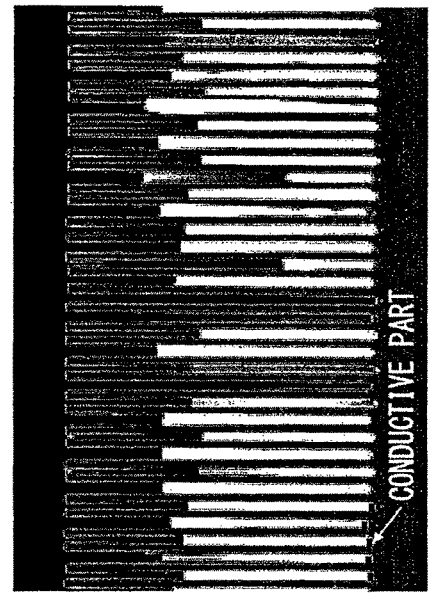
Figure 7C:
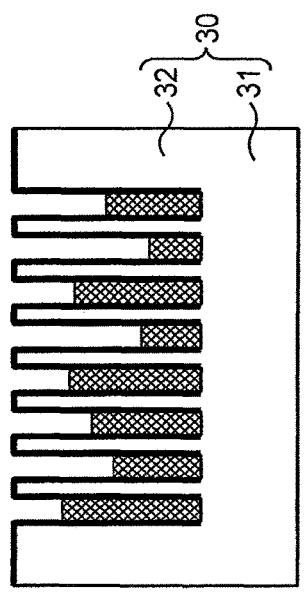

FIGS. 7A through 7D are diagrams for describing a difference in metal deposition in the case where an electroforming step is performed after a removing/surface area increasing step, and in the case where an electroforming step is performed after a removing step of removing only an insulating layer formed on a bottom part of a concave part. FIG. 7A is a diagram schematically showing a state of metal deposited in each of the slit grooves SD in the case where an electroforming step is performed after a removing/surface area increasing step, and FIG. 7B is an electron micrograph as an example of the above state. FIG. 7C is a diagram schematically showing a state of metal deposited in each of the slit grooves SD in the case where an electroforming step is performed after a removing step, and FIG. 7D is an electron micrograph as an example of the above state.

As shown in FIGS. 7A through 7D, metal is preferentially deposited on the bottom part of the slit groove SD by covering both side surfaces of the slit groove SD by the insulating layer 34 and by bringing the bottom part of the slit groove SD to an electrically conductive state. This is advantageous in effectively preventing formation of voids. Consequently, it is possible to finely form the metal parts 12b. However, as is obvious from the comparison between FIGS. 7A and 7B, and FIGS. 7C and 7D, in the case where an electroforming step is performed after a removing step (the case of FIGS. 7C and 7D), the metal deposition speed in the electroforming step may vary resulting from a slight difference in condition between slit grooves such as a surface area variation of the bottom part BT of the slit groove SD due to manufacturing error, or a variation in the degree of penetration of the plating solution 46. This may vary the deposition length of a metal part deposited in each of the slit grooves SD. Unlike the above configuration, in the case where an electroforming step is performed after a removing/surface area increasing step as described in the embodiment (the case of FIGS. 7A and 7B), it is possible to suppress a variation in metal deposition speed in the electroforming step by the surface area increasing effect of the conductive portion in the slit groove SD, and the deposition length of a metal part in each of the slit grooves SD is made substantially uniform. Accordingly, the metal grating structure DG manufacturing method according to the embodiment is advantageous in increasing the yield and in manufacturing a metal grating structure DG at a low cost.

In order to increase the surface area of the bottom part of the slit groove SD, according to an experiment result, it is empirically determined that the ratio between the depth H of the slit groove SD and the depth h of the deposition start tip concave part AP is preferably such that (depth H of slit groove SD):(depth h of deposition start tip concave part AP)=99:1 to 80:20, and more preferably such that (depth H of slit groove SD):(depth h of deposition start tip concave part AP)=95:5 to 85:15.

Both side surfaces (both side walls) of the deposition start tip concave part AP may be substantially vertical as with the case of the slit groove SD (a configuration such that a bottom surface and a side surface of the deposition start tip concave part AP perpendicularly intersect with each other, or a configuration such that a wall surface of the slit groove SD is flush with and continues to a wall surface of the deposition start tip concave part AP, or a configuration such that the angle defined by a wall surface of the slit groove SD and a wall surface of the deposition start tip concave part AP is substantially 180 degrees). However, in order to avoid formation of voids in the deposition start tip part 12bb, it is preferable, as described in the embodiment, to form both side surfaces (both side walls) of the deposition start tip concave part AP into a tapered shape (a configuration such that a bottom surface and a side surface of the deposition start tip concave part AP intersect obliquely with each other, or a configuration such that side surfaces of the deposition start tip concave part AP intersect with each other, or a configuration such that the angle defined by a wall surface of the slit groove SD and a wall surface of the deposition start tip concave part AP is smaller than 180 degrees).

FIGS. 8A through 8F are diagrams for describing a difference in metal deposition in an electroforming step due to a difference in sectional shape of a bottom part of a concave part. FIGS. 8A through 8C show a case, in which both side surfaces of a deposition start tip concave part APa have a tapered shape. FIG. 8A schematically shows a state of the deposition start tip concave part APa at the time when metal deposition is started. FIG. 8B schematically shows a state of the deposition start tip concave part APa during metal deposition. FIG. 8C schematically shows a state of the deposition start tip concave part APa at the time when metal deposition is ended. FIGS. 8D through 8F show a case, in which both side surfaces of a deposition start tip concave part APb extend vertically. FIG. 8D schematically shows a state of the deposition start tip concave part APb at the time when metal deposition is started. FIG. 8E schematically shows a state of the deposition start tip concave part APb during metal deposition. FIG. 8F schematically shows a state of the deposition start tip concave part APb at the time when metal deposition is ended. It is needless to say that metal deposition within the slit groove SD is carried out, following the end of metal deposition of the deposition start tip concave part AP (APa, APb) shown in FIG. 8C and FIG. 8F.

In the case where both side surfaces of the deposition start tip concave part APb extend substantially vertically, as shown in FIGS. 8D through 8F, the electric field intensity is slightly higher in the upper part of the deposition start tip concave part APb than in the bottom part thereof. Accordingly, the metal deposition speed is slightly faster in the upper part of the deposition start tip concave part APb than in the bottom part thereof. As a result, as shown in FIG. 8F via FIG. 8D and FIG. 8E, the upper part of the deposition start tip concave part APb may be clogged before the metal fills a space in the bottom part of the deposition start tip concave part APb, with the result that a void may be formed in the deposition start tip part 12bb. Unlike the above configuration, in the case where both side surfaces of the deposition start tip concave part APa have a tapered shape as described in the embodiment, as shown in FIG. 8C via FIG. 8A and FIG. 8B, it is possible to prevent formation of a void in the deposition start tip part 12bb. Accordingly, it is possible to regard the deposition start tip part 12bb as part of the grating part 12ba, and it is possible to design the metal grating structure DG in which the deposition start tip part 12bb and the grating part 12ba are integrally formed. In this way, the metal grating structure DG manufacturing method having the above configuration is advantageous in shortening a processing time, and makes it easy to form a slit groove SD by decreasing the depth H of the slit groove SD by the depth corresponding to the depth h of the deposition start tip concave part APa.

Even in the case where a void is formed in the deposition start tip part 12bb as shown in FIG. 8F, metal having an X-ray blocking function is finely deposited on the grating part 12ba with a sufficient thickness H without formation of a void, and it is possible to block X-ray substantially 100%. Accordingly, there is no likelihood that the performance of the metal grating structure DG is degraded. In the case where the metal grating structure DG is used as an X-ray diffraction grating in the above case, in order to avoid unexpected and unwanted X-ray scattering resulting from a void in the deposition start tip part 12bb, it is preferable not to form an X-ray incident surface on the deposition start tip part 12bb side but to form an X-ray incident surface on the side (the side where an opening of the slit groove SD was formed) of the grating part 12ba opposing to the deposition start tip part 12bb side.

On the other hand, in the case where a void is not formed in the deposition start tip part 12bb as shown in FIG. 8C, in use of the metal grating structure DG as an X-ray diffraction grating, an X-ray incident surface may be formed on the deposition start tip part 12bb side, or may be formed on the side (the side where an opening of the slit groove SD was formed) of the grating part 12ba opposing to the deposition start tip part 12bb side. In the case where metal is thickly deposited by an electroforming method, the surface (the surface of the grating part 12ba) of the metal part 12b is likely to be coarse. In view of the above, preferably, an X-ray incident surface may be formed on the deposition start tip part 12bb side, and more preferably, on the surface of the first silicon part 11 serving as an X-ray incident surface may be mirror-finished.

Further, in the metal grating structure DG manufacturing method according to the embodiment, the silicon substrate 30 is dry etched by a Bosch process. Accordingly, a side surface of the slit groove SD is made flat. This is advantageous in forming a metal grating structure DG with high precision. In particular, the above configuration is advantageous, because the incident surface or the exit surface is made flat in the case where the metal grating structure DG functions as a diffraction grating.

(Second Manufacturing Method)

In the first manufacturing method, a photosensitive resin layer (a photoresist layer) 33a is used as the resist layer 33. This is because a photosensitive resin layer has low resistance in the etching step and in the removing/surface area increasing step, and in view of a point that the resist layer 33 is etched or removed in these steps, it is necessary to have a relatively large film thickness. In view of the above, in the second manufacturing method, there is used a resist layer 33 made of a material having high resistance in an etching step and in a removing/surface area increasing step.

FIGS. 9A through 11D are diagrams for describing the second metal grating structure manufacturing method according to the embodiment. FIGS. 12A and 12B are diagrams for describing an insulating layer forming method by a vacuum vapor deposition method. FIG. 12A shows a first time film formation, and FIG. 12B shows a second time film formation.

Figure 9A:
FIGS. 9A through 9C are diagrams (part 1) for describing a second metal grating structure manufacturing method according to the embodiment.

In order to manufacture a metal grating structure DG according to the embodiment, at first, a silicon substrate 30 is prepared (see FIG. 9A). Preferably, the silicon substrate 30 is an n-type silicon substrate, in which most of the carriers are electrons.

Then, a resist layer 33 is formed on the principal plane of the silicon substrate 30 (a resist layer forming step). The resist layer 33 is patterned, and the patterned portion of the resist layer 33 is removed (a patterning step, see FIG. 9B, FIG. 9C, FIG. 10A, and FIG. 10B).

In the embodiment, the resist layer 33 may be made of the same material as the material of an insulating layer 34 described later. For instance, the resist layer 33 may be a silicon oxide film 33b having an insulating property and resistance in an etching process in an etching step that follows next. The silicon oxide film 33b is used as a patterned resist layer 33, and a photosensitive resist layer (a photoresist film) 40 is used for patterning the silicon oxide film 33b. In the case where the resist layer 33 and the insulating layer 34 are made of the same material as each other, the resist layer 33 (in this example, the silicon oxide film 33b) is formed to have a film thickness t1 larger than a film thickness t2 of the insulating layer 34 so that the resist layer 33 remains after an etching step that follows next and a removing/surface area increasing step described later.

Further, in the embodiment, the resist layer 33 may be made of a material different from the material of the insulating layer 34. For instance, the resist layer 33 may be a metal oxide film 33c having resistance in an etching process in the etching step, and having an insulating property and resistance in a removing process in the removing/surface area increasing step. An example of the metal oxide film 33c is an alumina film (an $Al_2O_3$ film). The metal oxide film 33c is used as a patterned resist layer 33, and the photosensitive resin layer 40 is used for patterning the metal oxide film 33c. In the above case, the metal oxide film 33c itself has resistance in an etching process in the etching step and a removing process in the removing/surface area increasing step. Accordingly, it is not necessary to make the film thickness t1 of the metal oxide film 33c larger than the film thickness t2 of the insulating layer 34. The metal oxide film 33c may have any film thickness, as far as the metal oxide film 33c has an electrically insulating property in an electroforming method.

The thus-configured silicon oxide film 33b and the thus-configured metal oxide film 33c serve as layers which have an insulating property and remain after an etching step and a removing/surface area increasing step.

Further, for instance, the resist layer 33 may be made of a material different from the material of the insulating layer 34. For instance, the resist layer 33 may be a metal film 33d having resistance in an etching process in the etching step and oxidizable. An example of the metal film 33d is an aluminum film (an Al film). The metal film 33d is used as a patterned resist layer 33, and a photosensitive resin layer 40 is used for patterning the metal film 33d. In the above case, a metal oxide film, preferably, an immobilized film having corrosion resistance in removing an oxide film 34 formed on a bottom surface BT of the structure, is formed on the top surface of the metal film 33d by thermal oxidation in an insulating film forming step described later. Thus, the metal film 33d acquires resistance in a process in the removing/surface area increasing step. Accordingly, it is not necessary to make the film thickness t1 of the metal film 33d larger than the film thickness t2 of the insulating layer 34, and the metal film 33d may have any film thickness, as far as the metal film 33d has an electrically insulating property in an electroforming method. In the above case, the metal film 33d may be such that a metal part remains in the inside of the metal oxide film, or the entirety of the metal film 33d may serve as a metal oxide film.

The oxidizable metal film 33d becomes a layer which has an insulating property by thermal oxidation in the insulating layer forming step, and which remains after an etching step and a removing step.

The resist layer 33 can be formed by various methods. More specifically, in the case where the resist layer 33 is a silicon oxide film 33b, the silicon oxide film 33b is formed on the surface of the silicon substrate 30 as the resist layer 33. The silicon oxide film 33b is formed to have the thickness t1 larger than the thickness t2 of the silicon oxide film 34 as the insulating layer 34 described later. The silicon oxide film 33b is formed by any of the well-known film forming methods such as a thermal oxidation method, a chemical vapor deposition (CVD) method, an anodic oxidation method, and a sputtering method. For instance, in the thermal oxidation method, an oxygen atmosphere (which may contain inert gas) or water vapor is introduced to a quartz tube in which the silicon substrate 30 is disposed, and the silicon substrate 30 is heated to a high temperature by heating the quartz tube by a heater in the oxygen atmosphere or in the gaseous atmosphere of water vapor, whereby the silicon oxide film 33b of a predetermined thickness (e.g. about 200 nm) is formed on the surface of the silicon substrate 30. Further, for instance, in the chemical vapor deposition (CVD) method, tetraethoxysilane (TEOS) as a kind of organic silanes is warmed, TEOS gas is generated by bubbling with use of carrier gas, and then, oxidation gas such as oxygen or ozone, and diluent gas such as helium gas are mixed with the TEOS gas, whereby raw material gas is generated. The thus generated raw material gas is introduced to a CVD apparatus such as a plasma CVD apparatus or an ozone CVD apparatus at a fixed temperature, whereby a silicon oxide film 33b of a predetermined thickness (for instance 200 nm) is formed on the surface of the silicon substrate 30 in the CVD apparatus. Further, for instance, in the anodic oxidization method, the positive pole of a power source is connected to the silicon substrate 30, and a cathode electrode connected to the negative pole of the power source and the silicon substrate 30 are immersed in an electrolytic solution. Then, supplying a current to the silicon substrate 30 in the above state forms a silicon oxide film 33b of a predetermined thickness (for instance about 200 nm) on the surface of the silicon substrate 30. The silicon oxide film 33b is formed at least on the upper surface of the silicon substrate 30, but may also be formed on the back surface or on a side surface of the silicon substrate 30. Use of the silicon oxide film 33b as the resist layer 33 as described above makes it possible to use the well-known film forming methods such as the thermal oxidation method, the chemical vapor deposition method, the anodic oxidation method, and the sputtering method. This makes it relatively easy to form a silicon oxide film 33b.

Figure 9B:
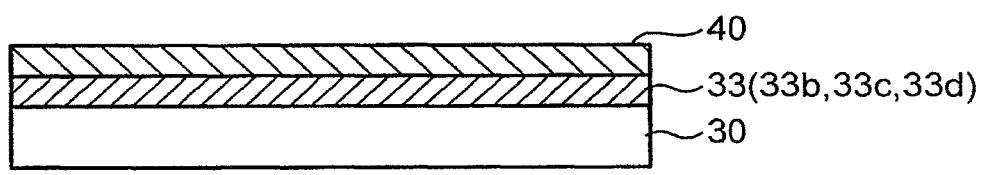
Figure 9C:
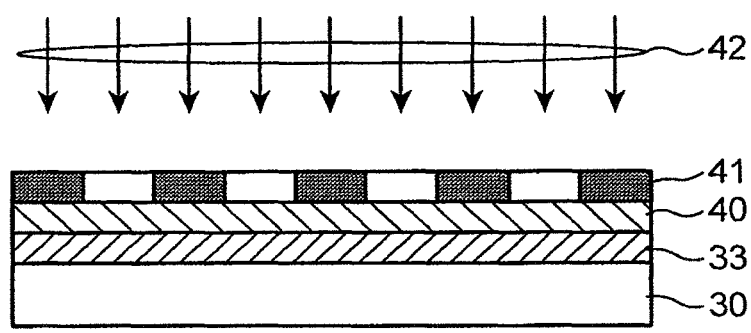

Subsequently, a photosensitive resin layer 40 is formed on the silicon oxide film 33b formed on the silicon substrate 30 by spin coating, for instance (see FIG. 9B). Subsequently, as a photolithography step, the photosensitive resin layer 40 is patterned by a lithography method (see FIG. 9C), and the patterned portion of the photosensitive resin layer 40 is removed (see FIG. 10A). More specifically, a lithography mask 41 is pressed against the photosensitive resin layer 40, ultraviolet light 42 is irradiated onto the photosensitive resin layer 40 via the lithography mask 41, and the photosensitive resin layer 40 is subjected to pattern exposure followed by development (see FIG. 9C). Then, the unexposed portion (or the exposed portion) of the photosensitive resin layer 40 is removed (see FIG. 10A).

Figure 10A:
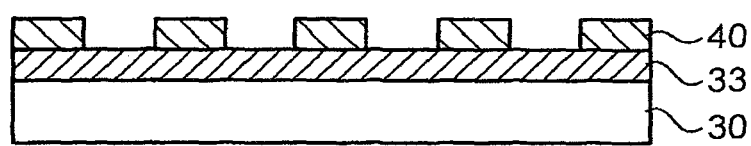
FIGS. 10A through 10C are diagrams (part 2) for describing the second metal grating structure manufacturing method according to the embodiment.
Figure 10B:
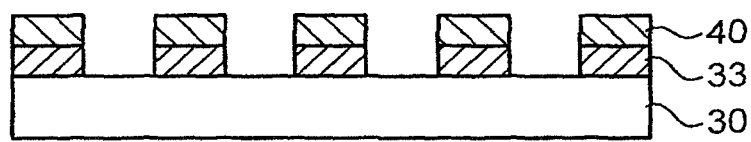
Figure 10C:
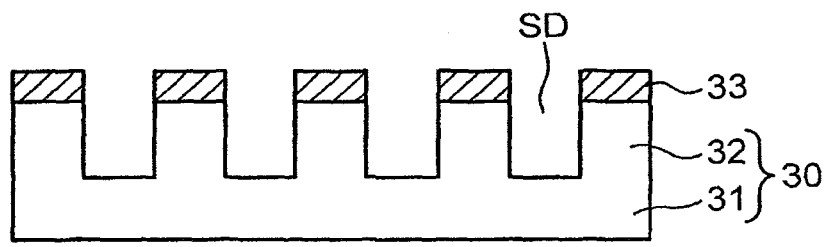

Subsequently, the silicon oxide film 33b is patterned by removing a portion of the silicon oxide film 33b where the photosensitive resin layer 40 is removed by etching, with use of the patterned photosensitive resin layer 40 as a mask (see FIG. 10B). More specifically, for instance, the silicon oxide film 33b is patterned by reactive etching (RIE) with use of $CHF_3$ gas. Further, for instance, the silicon oxide film 33b may be patterned by wet etching with use of hydrofluoric acid. The etching of the silicon oxide film 33b as the resist layer 33 in the patterning step may be performed by another etching method.

In the case where the metal oxide film 33c is used in place of the silicon oxide film 33b as the resist layer 33 in forming the silicon oxide film 33b as described above, the metal oxide film 33c is formed by a film forming method such as a chemical vapor deposition method or a sputtering method, for instance. Further, RIE with use of appropriate reactive gas is used in patterning the metal oxide film 33c in the patterning step. For instance, in the case where the metal oxide film 33c is an alumina film 33c, the alumina film 33c of about 150 nm in thickness is formed by a sputtering method, and then, the alumina film 33c is patterned by RIE with use of chlorine gas.

Further, in the case where a metal film 33d is used in place of the silicon oxide film 33b as the resist layer 33 in forming the silicon oxide film 33b as described above, the metal film 33d is formed by a film forming method such as a vacuum deposition method or a sputtering method. Further, RIE with use of appropriate reactive gas is used in patterning the metal film 33d in the patterning step. For instance, in the case where the metal film 33d is an aluminum film 33d, the aluminum film 33d of about 150 nm in thickness is formed by a sputtering method, and the aluminum film 33d is patterned by RIE with use of chlorine gas.

Then, the portion of the silicon substrate 30 where the photosensitive resin layer 40 and the resist layer 33 are removed by a dry etching method are etched to a first predetermined depth H in the normal direction Dz. By performing the above treatment, a slit groove SD is formed (see FIG. 10C, an etching step).

More specifically, the silicon substrate 30 is etched by ICP (Inductively Coupled Plasma) dry etching to the first predetermined depth H from the surface of the silicon substrate 30, with use of the patterned photosensitive resin layer 40 and the patterned resist layer 33 as masks. The ICP dry etching is preferably an ASE process by an ICP apparatus, and more preferably, a Bosch process. The dry etching method is not limited to the ICP dry etching, but any other technique as described above may be applied.

By the ICP dry etching, the photosensitive resin layer 40 is removed. The resist layer 33 may be slightly etched. In the foregoing example, in the case where the resist layer 33 is a silicon oxide film 33b, the thickness of the silicon oxide film 33b decreases from about 200 nm to about 170 nm by ICP dry etching. Further, in the case where the resist layer 33 is a metal oxide film 33c, specifically, an alumina film 33c, the thickness of the alumina film 33c decreases from about 150 nm to about 130 nm by ICP dry etching, for instance. Further, in the case where the resist layer 33 is a metal film 33d specifically, an aluminum film 33d, the thickness of the aluminum film 33d decreases from about 150 nm to about 130 nm by ICP dry etching, for instance.

A plate like part (a layer like part or a wall part) 32 of the silicon substrate 30 that remains along the DxDz plane after the etching serves as a second silicon part 12a, and a plate like part (a base part) 31 of the silicon substrate 30 that remains along the DxDy plane after the etching serves as a first silicon part 11.

Subsequently, an insulating layer 34 of a predetermined thickness is formed over the entirety of the inner surface of the slit groove SD in the silicon substrate 30 by a thermal oxidation method to have an insulating property in an electroforming method in an electroforming step described later (see FIG. 10A, an insulating layer forming step). The insulating layer 34 is a silicon oxide film 34b because the silicon substrate 30 is used. The silicon oxide film 34b as the insulating layer 34 is formed to have a thickness of about 40 nm, for instance. The silicon oxide film 34b is formed at least on the inner surface of the slit groove SD in the silicon substrate 30, but may also be formed on the back surface or on a side surface of the silicon substrate 30. The thermal oxidation method is such that an oxide film is deposited and formed on a surface of a target material to be oxidized (in this embodiment, the inner surface of a concave part of the silicon substrate 30) by heating the target material in a gaseous atmosphere of oxygen or water vapor. Accordingly, it is possible to obtain a very fine oxide film having a desired adhesiveness to the material. Further, the thermal oxidation method is advantageous in precisely controlling the film thickness by adjusting the flow rate of a gaseous atmosphere or the heating time of a gaseous atmosphere. This makes it easy to obtain oxide films in a film thickness range from a film thickness of several nm to a film thickness of micron order. Accordingly, the thermal oxidation method is appropriate as a method for forming an insulating layer 34 in an electroforming method in an electroforming step.

More specifically, in the case where the resist layer 33 is a silicon oxide film 33b, for instance, a silicon oxide film 34b of a substantially uniform thickness was formed over the entirety of the inner surface of a slit groove of about 40 nm in depth by heating the silicon substrate 30 in an atmosphere of oxygen to be introduced at a flow rate of 200 ml/min at 1,000° C. for sixty minutes. Further, for instance, a silicon oxide film 34b of a substantially uniform thickness was formed over the entirety of the inner surface of a slit groove of about 40 nm in depth by heating the silicon substrate 30 in an atmosphere of water vapor to be introduced at a flow rate of 1 liter/min at 1,150° C. for four minutes.

Further, in the case where the resist layer 33 is a metal oxide film 33c (in this example, an alumina film 33c), a silicon oxide film 34b of a substantially uniform thickness was formed over the entirety of the inner surface of a slit groove of about 40 nm in depth by heating the silicon substrate 30 in an atmosphere of water vapor to be introduced at a flow rate of 1 liter/min at 1,150° C. for four minutes.

Further, in the case where the resist layer 33 is a metal film 33d (in this example, an aluminum film 33d), a silicon oxide film 34b of a substantially uniform thickness was formed over the entirety of the inner surface of a slit groove of about 40 nm in depth by heating the silicon substrate 30 in an atmosphere of oxygen to be introduced at a flow rate of 200 ml/min at 1,000° C. for sixty minutes.

In the case where the resist layer 33 is a silicon oxide film 33b or a metal oxide film 33c, an oxide film is hardly formed on the surface of the resist layer 33 by thermal oxidation in the insulating layer forming step. In the foregoing example, in the case where the resist layer 33 is a silicon oxide film 33b, the thickness of the silicon oxide film 33b increased from about 170 nm to about 180 nm by thermal oxidation in the insulating layer forming step. In the case where the resist layer 33 is an alumina film 33c, the thickness of the alumina film 33c increased from about 130 nm to about 140 nm by thermal oxidation in the insulating layer forming step.

On the other hand, in the case where the resist layer 33 is a metal film 33d, a metal oxide film 34d is formed on the surface of the metal film 33d by thermal oxidation in the insulating layer forming step. Thus, the metal film 33d as the resist layer 33 acquires resistance in a removing process in a removing step, and acquires an insulating property in an electroforming method in an electroforming step. In the case where the metal film 33d is an aluminum film, an alumina film as an immobilized film is formed. In the foregoing example, an alumina film 34d of about 80 nm in thickness was formed.

In the foregoing, a thermal oxidation method is used for forming an insulating layer 34 in the insulating layer forming step. Alternatively, an anodic oxidation method or a deposition method may be used.

In the anodic oxidization method, the insulating layer 34 is a silicon oxide film 34b, because the silicon substrate 30 is used. The silicon oxide film 34b as the insulating layer 34 is formed to have a thickness of about 20 nm, for instance. More specifically, in order to perform anodic oxidation, the silicon substrate 30 is connected to the positive pole of a power source, and a cathode electrode connected to the negative pole of the power source and the silicon substrate 30 are immersed in an electrolytic solution. When a current is supplied to the silicon substrate 30 in the above state, a silicon oxide film 34b of a predetermined thickness is formed on the surface of the silicon substrate 30, and an insulating layer 34 is formed (see FIG. 11A). The silicon oxide film 34b is formed at least on the inner surface of a slit groove SD of the silicon substrate 30, but may also be formed on the back surface or on a side surface of the silicon substrate 30.

The anodic oxidation method is a method such that a conductive material (in this embodiment, the silicon substrate 30) to be oxidized is immersed in an electrolytic solution, and a current is supplied to the material as an anode (a positive pole or a plus pole) so that oxygen in the electrolytic solution is bonded to the surface of the material for depositing and forming an oxide film on the surface of the material. In this example, in the case where an electrolytic solution to be used does not dissolve an oxide film formed on the surface of the material, or the solubility of the electrolytic solution is small, it is possible to form a very fine oxide film having a desired adhesiveness to the material, because the anodic oxidation method accelerates the film formation as described above. Further, in the anodic oxidation method, oxidation is accelerated and oxidized matter formed on the surface of the material inhibits conduction to thereby stop the acceleration of oxidation. Accordingly, even if there are formed a portion where oxidation is accelerated and a portion where oxidation is retarded during the oxidation, by continuing current supply, the portion where oxidation is retarded can be oxidized by the same film thickness as the other portion where oxidation has been completed by the time when the oxidation is terminated. Accordingly, the anodic oxidation method is advantageous in forming an oxide film having uniform fineness and uniform film thickness over the entirety of the surface of the material at the final stage of processing. Further, in the anodic oxidation method, a film thickness of an oxide film is proportional to an applied voltage. Accordingly, by adjusting the applied voltage, it is possible to finely control the film thickness. Thus, it is easy to obtain oxide films in a film thickness range from a film thickness of several nm to a film thickness of several μm. As described above, the anodic oxidation method is appropriate as a method for forming an insulating layer 34 in an electroforming method in an electroforming step.

In the case where the inner surface of a slit groove of the silicon substrate 30 is subjected to anodic oxidation, the electrolytic solution is preferably an acidic solution which has strong oxidation power but does not dissolve an oxide film formed by anodic oxidization, for instance, a solution of nitric acid, hydrochloric acid, sulfuric acid, oxalic acid, or phosphoric acid. Further, it is possible to use a solution of neutral salt such as ammonium borate, ammonium tartarate, or ammonium citrate. In the case where the resist layer 33 is a metal film 33d, for instance, an aluminum film 33d, the electrolytic solution is a solution containing acid having strong oxidation power but anti-corrosive against aluminum oxide such as boric acid; or a solution containing acid having weak oxidation power and less corrosive against aluminum oxide, such as dilute oxalic acid or dilute phosphoric acid; or a solution containing neutral salt such as ammonium borate, ammonium tartarate, or ammonium citrate.

The cathode electrode is preferably made of a metal that does not dissolve in the electrolytic solution, for instance, gold (Au) or platinum (Pt).

More specifically, in the case where the resist layer 33 is a silicon oxide film 33b, for instance, immersing the silicon substrate in a nitric acid aqueous solution of 68% in concentration, and applying a voltage of 40V to the silicon substrate with use of a platinum cathode electrode results in termination of current supply substantially after lapse of 15 minutes, and a silicon oxide film 33b of a substantially uniform film thickness was formed over the entirety of the inner surface of a slit groove of about 20 nm in depth.

Further, in the case where the resist layer 33 is a metal oxide film 33c (in this example, an alumina film 33c), immersing the silicon substrate in a hydrochloric acid aqueous solution of 35% in concentration, and applying a voltage of 40V to the silicon substrate with use of a platinum cathode electrode results in termination of current supply substantially after lapse of 15 minutes, and a silicon oxide film 33a of a substantially uniform film thickness was formed over the entirety of the inner surface of a slit groove of about 20 nm in depth.

Further, in the case where the resist layer 33 is a metal film 33d (in this example, an aluminum film 33d), immersing the silicon substrate in an oxalic acid aqueous solution of 0.5 mol % in concentration, and applying a voltage of 40V to the silicon substrate with use of a platinum cathode electrode results in termination of current supply substantially after lapse of 10 minutes, and a silicon oxide film 33a of a substantially uniform film thickness was formed over the entirety of the inner surface of a slit groove of about 20 nm in depth, and an alumina film of about 55 nm in thickness was formed on the surface of the aluminum film 33d.

In this example, in the case where the resist layer 33 is a silicon oxide film 33b or a metal oxide film 33c, an oxide film is hardly formed on the surface of the resist layer 33 by anodic oxidation in the insulating layer forming step. On the other hand, in the case where the resist layer 33 is a metal film 33d, as described above, a metal oxide film 34d is formed on the surface of the resist layer 33 by anodic oxidation in the insulating layer forming step. Accordingly, the metal film 33d as the resist layer 33 acquires resistance in a removing process in a removing step, and acquires an insulating property in an electroforming method in an electroforming step. In the case where the metal film 33d is an aluminum film, an alumina film as an immobilized film is formed. In the foregoing example, an alumina film 34d of about 55 nm in thickness was formed. Further, immersing the silicon substrate in an oxalic acid aqueous solution of 0.5 mol % in concentration, and applying a voltage of 40V to the silicon substrate with use of a platinum cathode electrode results in formation of an alumina film of about 30 nm in thickness after lapse of about 5 minutes.

Further, a deposition method is a film formation method for forming an insulating layer 34, using a deposition action. Examples of the deposition method are a chemical vapor deposition method, a sputtering method, and a vacuum vapor deposition method. Examples of the insulating layer 34 to be formed by the deposition method are a silicon oxide film 34b and a metal oxide film 34c. An example of the metal oxide film 34c is an alumina film 34c. The insulating layer 34 is formed on the principal plane of the silicon substrate 30 where a slit groove SD is formed by a deposition method. Accordingly, the insulating layer 34 is formed over the entire surface of the principal plane. In other words, the insulating layer 34 is formed over the inner surface of a slit groove SD (a wall surface (inner side surfaces) and a bottom surface of the slit groove SD), and on an upper surface part (an apex part) of a wall part of the silicon substrate 30 which constitutes the slit groove SD and remains in the etching step. The insulating layer 34 may also be formed on the back surface or on a side surface of the silicon substrate 30.

The deposition method makes it possible to form a film by using a deposition action. Accordingly, the deposition method is advantageous in forming a fine film. Thus, the deposition method is appropriate as a method for forming an insulating layer 34 by an electroforming method in an electroforming step.

More specifically, in the case where an insulating layer 34 is deposited and formed by a chemical vapor deposition method over the entire surface on the principal plane of the silicon substrate 30 where a slit groove SD is formed, for instance, as described above, tetraethoxysilane (TEOS) is warmed, TEOS gas is generated by bubbling with use of carrier gas, and then, oxidation gas such as oxygen or ozone, and diluent gas such as helium gas are mixed with the TEOS gas, whereby raw material gas is generated. The thus generated raw material gas is introduced to a CVD apparatus such as a plasma CVD apparatus or an ozone CVD apparatus at a fixed temperature, whereby a silicon oxide film 34*b* of a predetermined thickness (for instance, about 40 nm) is formed on the surface of the silicon substrate 30 in the CVD apparatus. In this example, an alumina film 34*b* of a predetermined thickness (for instance, about 30 nm) is formed as the insulating layer 34 by CVD with use of aluminium isopropoxide, in place of tetraethoxysilane. The CVD is a surface chemical reaction of raw gas. Accordingly, it is relatively easy to form a fine film on the inner wall of a structure (on the inner surface of a slit groove SD in the embodiment) with a film thickness of from several nm to several μm, without applying a special treatment.

Further, in the case where an insulating layer 34 is deposited and formed by a sputtering method over the entire surface on the principal plane of the silicon substrate 30 where a slit groove SD is formed, a target material (for instance, quartz or alumina) to be deposited and formed as the insulating layer 34 is placed in a vacuum chamber, and a high voltage is applied to the target material. As a result of applying a high voltage, a rare-gas element (ordinarily, argon gas) such as ionized argon gas is irradiated and collides against the target material. By the collision, atoms on the surface of the target material are sputtered. When the sputtering atoms (sputtering particles) impinge on the surface of the principle plane, the sputtering particles are deposited on the surface of the principle plane, and a film is formed. It is preferable to enhance the directionality of sputtering particles by disposing the target material and the silicon substrate 30 away from each other by a predetermined distance of about 100 mm in order to allow the sputtering particles to impinge on the bottom part BT and to form a uniform and fine film on the inner surface of a slit groove SD of a high aspect ratio. Further, mixing a trace amount of nitrogen gas in rare gas such as ionized argon gas results in formation of a thin lubricant film of nitrogen near the opening of a slit groove SD. This is more preferable, because the sputtering particles easily impinge on the bottom part BT of the slit groove SD while sliding along the lubricant film. The sputtering method makes it relatively easy to form a fine film on the inner wall of a structure (on the inner surface of a slit groove SD in this embodiment) with a film thickness of from several nm to several μm by appropriately setting a condition such as extending the time for film formation, increasing the voltage for ionizing rare gas, or increasing the number of sputtering particles.

Further, in the case where an insulating layer 34 is deposited and formed by a vacuum vapor deposition method over the entire surface on the principal plane of the silicon substrate 30 where a slit groove SD is formed, the silicon substrate 30 is disposed in a vacuum chamber at such a position as to face a material (a vapor deposition source) to be deposited and formed as the insulating layer 34, and a film forming material (a vapor deposition material) in a gaseous state generated by heating the vapor deposition source is supplied to the surface of the principal plane of the silicon substrate 30. Impinging the vapor deposition material on the surface of the principal plane of the silicon substrate 30 results in deposition of the vapor deposition material and film formation on the surface of the principal plane of the silicon substrate 30. The vacuum vapor deposition method is ordinarily carried out in a low atmospheric pressure of about $10^{-2}$ to $10^{-4}$ Pa. Accordingly, the average free path of the vapor deposition material is as long as about several ten centimeters to several ten meters, and the vapor deposition material impinges on the silicon substrate 30 substantially without collision. Thus, the vapor deposition material vaporized from the vapor deposition source has a very good directionality. Accordingly, it is possible to uniformly and finely process the inner surface of a slit groove SD of a relatively high aspect ratio to the position deep inside the slit groove SD. Further, in the vacuum vapor deposition method, the directionality of the vapor deposition material is extremely high. Accordingly, in the case where it is difficult to form a film on the inner side surface of a slit groove SD, as shown in FIG. 12A, a first time film formation is performed with respect to the silicon substrate 30 including a side surface thereof by slightly inclining the silicon substrate 30 with respect to the vapor deposition source, and subsequently, as shown in FIG. 12B, a second time film formation is performed with respect to the silicon substrate 30 by inclining the silicon substrate 30 in the direction opposite to the direction in the first time film formation. By performing the above operation, it is possible to form a film on both side surfaces of the slit groove SD. Further, in order to form an insulating layer 34 with enhanced fineness and strength, ion-beam assisted deposition (IAD) of emitting gaseous ions of about several 100 eV on a substrate may be performed with use of an ion beam gun during vacuum vapor deposition. As described above, the vacuum vapor deposition method also makes it relatively easy to form a fine film on the inner wall of a structure (on the inner surface of a slit groove SD in the embodiment) with a film thickness of from several nm to several μm.

The following is the combinations of the resist layer 33 and the insulating layer 34 in each of the steps. In the case where the resist layer 33 is a silicon oxide film 33*b* formed by one of the film formation methods i.e. the thermal oxidation method, the anodic oxidation method, and the deposition method, there are proposed a configuration 1A, in which the insulating layer 34 is a silicon oxide film 34*b* (in the case of CVD, TEOS) formed by one of the film formation methods i.e. the thermal oxidation method, the anodic oxidation method, and the deposition method; and a configuration 1B, in which the insulating layer 34 is an alumina film 34*c* formed by the deposition method. In the case where the resist layer 33 is an alumina film 33*c* formed by the deposition method, there are proposed a configuration 2A, in which the insulating layer 34 is a silicon oxide film 34*b* (in the case of CVD, TEOS) formed by one of the film formation methods i.e. the thermal oxidation method, the anodic oxidation method, and the deposition method; and a configuration 2B, in which the insulating layer 34 is an alumina film 34*c* formed by the deposition method. In the case where the resist layer 33 is an aluminum film 33*d* formed by the deposition method, there is proposed a configuration 3A, in which the insulating layer 34 is a silicon oxide film 34*b* formed by one of the film formation methods i.e. the thermal oxidation method and the anodic oxidation method.

Referring back to FIGS. 11A through 11D, the surface area of the bottom part of the slit groove SD is increased as compared with a state before the etching by removing a portion of the insulating layer 34 formed on the bottom part BT of the slit groove SD, and by etching the plate like part (the base part) 31 of the silicon substrate 30 at the bottom part BT of the slit groove SD (a removing/surface area increasing step, namely, a removing step shown in FIG. 11B, and a surface area increasing step shown in FIG. 11C).

Figure 11A:
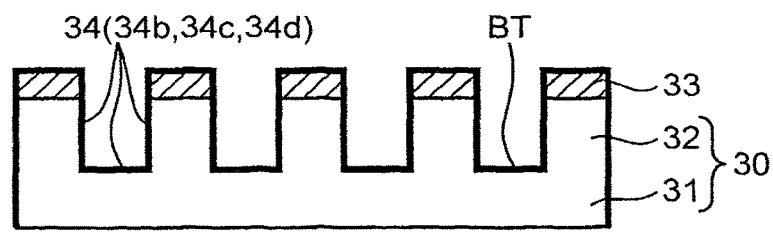
FIGS. 11A through 11D are diagrams (part 3) for describing the second metal grating structure manufacturing method according to the embodiment.
Figure 11B:
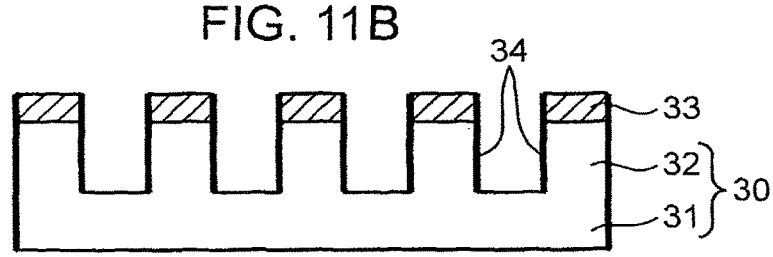
Figure 11C:
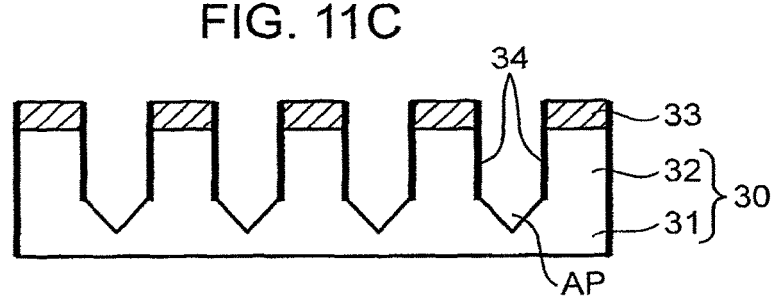
Figure 12A:
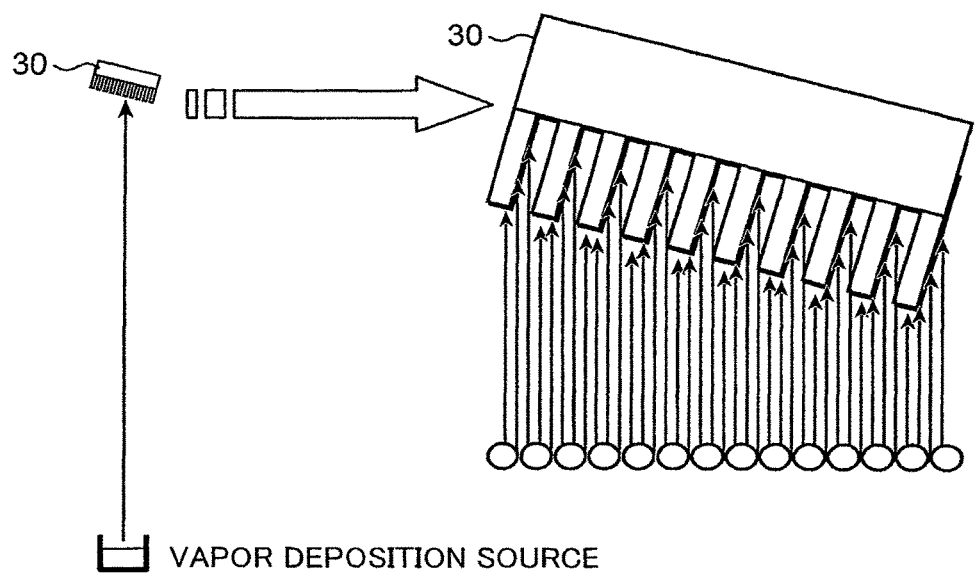
FIGS. 12A and 12B are diagrams for describing an insulating layer forming method by a vacuum vapor deposition method.
Figure 12B:
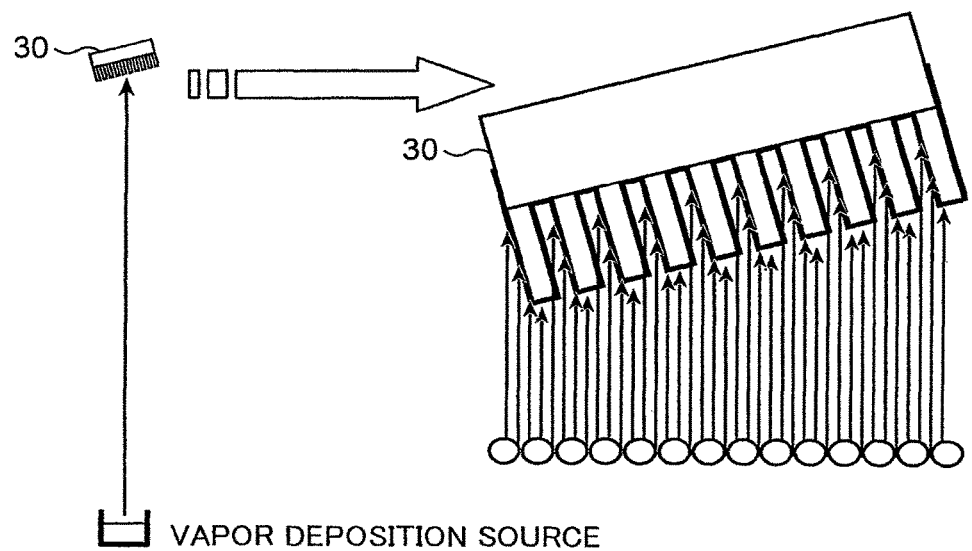

More specifically, as well as the first manufacturing method, in the removing step, a portion of an insulating layer 34 formed on a bottom part BT of a slit groove SD by ICP dry etching with use of $CHF_3$ gas is etched and removed (see FIG. 11B). Subsequently, in the surface area increasing step, gas suitable for etching a silicon substrate, for instance, $SF_6$ gas is used, and a plate like part (a base part) 31 of the silicon substrate 30 at the bottom part BT of the slit groove SD is etched by ICP dry etching with use of the $SF_6$ gas (see FIG. 11C). For instance, by a process similar to a Bosch process as described above, the base part 31 of the silicon substrate 30 is etched to such an extent that the side surfaces of a deposition start tip concave part AP have a tapered shape. Further, for instance, a (100) substrate is selected as the silicon substrate 30, and a slit groove SD is formed so that the longitudinal direction of the slit groove SD coincides with [110] direction. Further, the base part 31 of the silicon substrate 30 is etched so that the side surfaces of the deposition start tip concave part AP have a tapered shape by subjecting the silicon substrate 30 to anisotropic etching with use of an etching solution such as a solution of potassium hydroxide or TMAH (tetramethylammonium hydroxide). By the aforementioned surface area increasing step, for instance, the base part 31 of the silicon substrate 30 is etched by 1,000 nm.

In the case where the resist layer 33 is a silicon oxide film 33b, the silicon oxide film 33b as the resist layer 33 is also etched on a wall part 32 (on an apex part of a wall part 32) of the silicon substrate corresponding to a second silicon part 12a by ICP dry etching with use of $CHF_3$ gas. However, the thickness t1 of the silicon oxide film 33b after the patterning is larger than the thickness t2 of the silicon oxide film 34b as the insulating layer 34 (t1>t2). Accordingly, at the point of time when a portion of the silicon oxide film 34b as the insulating layer 34 formed on the bottom part BT of the slit groove SD is removed, the silicon oxide film 33b as the insulating layer 33 remains. In the foregoing example, although the thickness of the silicon oxide film 33a is reduced from 170 nm to 100 nm, the silicon oxide film 33a securely remains.

Further, in the case where the resist layer 33 is a metal oxide film (e.g. an alumina film) 33c, the metal oxide film 33c as the resist layer 33 is hardly etched on a wall part 32 (on an apex part of a wall part 32) of the silicon substrate corresponding to a second silicon part 12a by ICP dry etching with use of $CHF_3$ gas. In the foregoing example, even after the part BT of the silicon oxide film 34c (the insulating layer 34) of 20 nm in thickness formed on the bottom part of the slit groove SD is removed by ICP dry etching in the removing step, the alumina film 33c is hardly etched and remains, although the thickness of the alumina film 33c is reduced from about 130 nm to about 125 nm.

Further, in the case where the resist layer 33 is a metal film (e.g. an aluminum film) 33d, a metal oxide film (in this example, an alumina film) is formed on the top surface of the resist layer 33 by thermal oxidation in the insulating layer forming step. Accordingly, the metal film 33d as the insulating layer 33 is hardly etched due to the existence of the metal oxide film on the wall part 32 (on the apex part of the wall part 32) of the silicon substrate corresponding to the second silicon part 12a by ICP dry etching with use of $CHF_3$ gas. In the foregoing example, the alumina film formed on the aluminum film 33d is hardly etched and remains, although the alumina film is etched by about 5 nm in thickness by ICP dry etching in the removing step.

In the case where the insulating layer 34 is an alumina film 34c or 34d, ICP dry etching is performed by using chlorine-based gas containing boron such as $BCl_3$ gas capable of etching alumina.

The resist layers 33 on the upper surfaces (apex parts) of the second silicon parts 12a, which remain after the removing/surface area increasing step, serve as the second insulating layers 12d.

The silicon substrate 30 which has undergone the resist layer forming step, the patterning step, the etching step, the insulating layer forming step, and the removing/surface area increasing step in this order serves as an intermediate product for a metal grating structure.

Figure 11D:
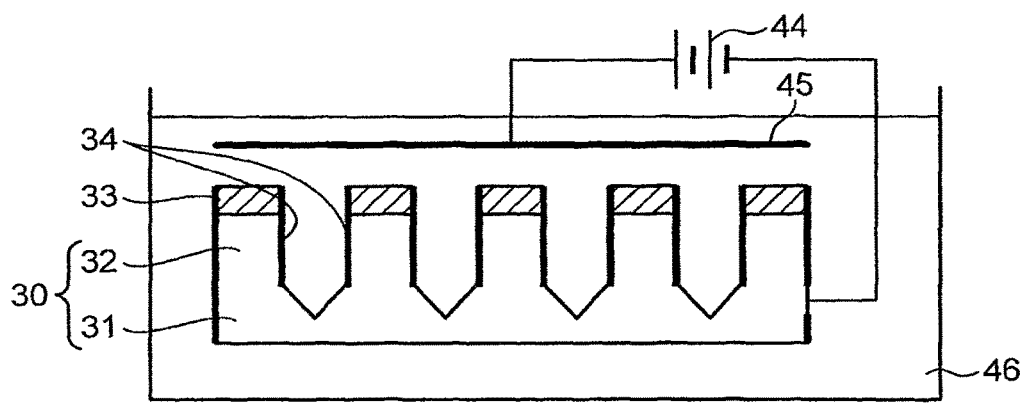

Subsequently, the slit groove SD is filled with metal by applying a voltage to the silicon substrate 30 by an electroforming method (an electroplating method) (an electroforming step, see FIG. 11D). More specifically, as well as the first manufacturing method, the negative pole of a power source 44 is connected to the silicon substrate 30, and an anode electrode 45 connected to the positive pole of the power source 44 and the silicon substrate 30 are immersed in a plating solution 46. By performing the above treatment, metal is precipitated and deposited on the silicon substrate 30 (a plate like part 31) side at a deposition start tip concave part AP communicating with a slit groove SD by electroforming. Then, when the metal fills the deposition start tip concave part AP and the slit groove SD, the electroforming is ended. By performing the above treatment, the metal fills the deposition start tip concave part AP, and is deposited by the same thickness H as the plate like part 32 of the silicon substrate 30. In this way, metal is filled in a deposition start tip concave part AP and in a slit groove SD, and a deposition start tip part 12bb and a grating part 12ba of a metal part 12b are formed.

The metal grating structure DG having the configuration as shown in FIG. 1 is manufactured by performing the above manufacturing steps.

The second manufacturing method provides substantially the same effects as the first manufacturing method. The second manufacturing method is also advantageous in finely forming the metal parts of a grating structure by an electroforming method. In the above configuration, the surface area of the silicon substrate 30 to be exposed increases by the removing/surface area increasing step. As a result, the electrically conductive surface area in the electroforming step increases. This is advantageous in suppressing a variation of metal deposition speed in each of the slit grooves SD. Thus, the second metal grating structure DG manufacturing method according to the embodiment is advantageous in manufacturing a metal grating structure DG having a substantially uniform deposition length of a metal part in each of the slit grooves SD by an electroforming method.

JP 2010-185728A discloses a method for manufacturing a diffraction grating for an X-ray Talbot interferometer with use of a silicon substrate. The method for manufacturing a diffraction grating for an X-ray Talbot interferometer disclosed in the above publication includes:

a groove forming step of alternately repeating an etching step of forming a concave part by performing preferential reactive ion etching to a silicon substrate with use of gas containing F atoms in an inductively coupled plasma processing apparatus, and a protective film deposition step of depositing a polymer film, as a protective film, on a bottom surface and side wall surfaces of the concave part by introducing fluorocarbon-based gas in the inductively coupled plasma processing apparatus;

a silicon oxide film forming step of forming an electrically insulating film constituted of a silicon oxide film on a bottom surface and side wall surfaces of the groove by introducing oxygen gas in the inductively coupled plasma processing apparatus;

a silicon exposing step of removing a portion of the electrically insulating film on the bottom surface of the groove, and exposing a silicon portion of the silicon substrate on the bottom surface by performing reactive ion etching with use of gas containing F atoms in the inductively coupled plasma processing apparatus; and an electroplating step of subjecting the exposed surface of the silicon portion as a seed layer to electroplating to precipitate an X-ray absorbing metal part in the groove.

In the case where an electrically insulating film constituted of a silicon oxide film to be formed on a bottom surface and side wall surfaces of the groove in the silicon oxide film forming step in the aforementioned method for manufacturing a diffraction grating for an X-ray Talbot interferometer is formed by introducing oxygen in an inductively coupled plasma processing apparatus, the thickness of the electrically insulating film is at most about 2 nm, referring to a non-patent literature cited in the aforementioned publication i.e. "development of new deep RIE technology using dual side wall protective film" by Junji Ohara and other five persons, Denso Technical Review issued by Denso Corporation in the year of 2000, pp. 45-50, Vol. 5, No. 1, 2000". It seems to be difficult to further increase the thickness of the film, even if a discharge condition relating to plasma processing, or parameters such as a flow rate of oxygen or a time for irradiating oxygen is changed. Although the aforementioned film may function as a mask for reactive ion etching in the silicon exposing step in the aforementioned publication, the film has such a small thickness as described above, and does not have sufficient fineness for actual use. Accordingly, the aforementioned film may not sufficiently function as the electrically insulating film in the electroplating step in the aforementioned publication, and does not function as an appropriate film in the electroplating step. Since the entirety of a silicon substrate is electrically conductive, X-ray absorbing metal may also be deposited on the side wall surfaces of the groove in the electroplating step. As a result, a hollow portion (a void i.e. a portion in which metal is not filled) may be generated in the X-ray absorbing metal part. It is technically difficult to finely fill the groove with the X-ray absorbing metal by electroplating.

As described above, according to the embodiment, in the insulating layer forming step, an insulating layer 34 is formed on the inner surface of a slit groove SD in the silicon substrate 30 by one of the deposition method, the thermal oxidation method, and the anodic oxidation method. Accordingly, in the metal grating structure DG manufacturing method according to the embodiment, it is possible to form an insulating layer 34 having enhanced fineness and a predetermined film thickness capable of securing electrical insulation in an electroforming method in an electroforming step. Thus, the embodiment is advantageous in securing electrical insulation in an electroforming method in an electroforming step.

Specifically, in the case where a deposition method such as a chemical vapor deposition method, a sputtering method, or a vapor deposition method is used, the deposition method is advantageous in forming an insulating layer having enhanced fineness, and also makes it relatively easy to control the film thickness. In the case where a thermal oxidation method is used, the thermal oxidation method is advantageous in forming a silicon oxide film having enhanced fineness and adhesiveness, and also makes it relatively easy to control the film thickness. In the case where an anodic oxidation method is used, the anodic oxidation method is advantageous in forming a silicon oxide film having enhanced fineness, adhesiveness, and uniformity in film thickness, and also makes it relatively easy to control the film thickness. Accordingly, the metal grating structure manufacturing method having the above configuration is advantageous in forming a fine insulating layer of a predetermined film thickness capable of securing electrical insulation in an electroforming method in an electroforming step.

Further, in the first manufacturing method, the resist layer 33 (a photosensitive resin layer 33a) is formed to have a certain thickness after the etching step and the removing/surface area increasing step. Accordingly, the resist layer 33 securely remains, regardless of etching and removing in the respective processes in the etching step and in the removing/surface area increasing step.

Further, in the second manufacturing method, in the case where the resist layer 33 and the insulating layer 34 are made of the same material, for instance, composed of silicon oxide films 33b and 34b, or alumina films 33c and 34c, the resist layer 33 is formed to have a thickness larger than the thickness of the insulating layer 34 so that the resist layer 33 remains after the etching step and the removing/surface area increasing step. Accordingly, the resist layer 33 securely remains after the removing step, regardless of removal in a removing process in the removing/surface area increasing step.

On the other hand, in the second manufacturing method, in the case where the resist layer 33 and the insulating layer 34 are made of materials different from each other, in other words, in the case where the resist layer 33 is made of a material different from the material of the insulating layer 34 such that the resist layer 33 has resistance in an etching process in the etching step, has resistance in a removing process in the removing step, and has an insulating property in the electroforming step, it is possible to preferentially remove the insulating layer 34 in the removing step, and the resist layer 33 remains after the removing step. In this way, forming the resist layer 33 and the insulating layer 34 of materials different from each other makes it possible to form the resist layer 33 and the insulating layer 34 of materials different from each other in the etching rate. Thus, the above configuration is advantageous in preferentially removing the part BT of the insulating layer 34 formed on the bottom part of the slit groove SD.

According to the first and second metal grating structure DG manufacturing methods, an apex part (an upper surface) of a wall part 32 of the silicon substrate 30 (each of the plate like parts 32 of the silicon substrate 30) which constitutes a slit groove SD and remains in the etching step is also insulated in the electroforming method in the electroforming step. Accordingly, the wall part securely acquires an insulating property in the electroforming method by cooperation of the insulating layer 34 with the resist layer 33 that remains.

In JP 2010-185728A, the etching mask to be used in the etching step (a groove forming step) is a photoresist mask (see the paragraph [0044] of the above publication). Accordingly, the photoresist mask that remains after the etching step on the apex part (on one surface of the silicon substrate) of the wall part of the silicon substrate (a remaining portion of the silicon substrate after the etching) that constitutes the side wall surfaces of the groove, reacts with oxygen in the silicon oxide film forming step, and it is highly likely that the photoresist mask does not remain in the electroplating step. The entirety of the silicon substrate is electrically conductive. Accordingly, in the electroplating step, it is highly likely that X-ray absorbing metal is also deposited on an apex part of a wall part of the silicon substrate, and as a result, a hollow portion (a void or a portion in which metal is not filled) may be formed in the X-ray absorbing metal part. Unlike the above configuration, in the metal grating structure DG manufacturing method according to the embodiment, as described above, the resist layer 33 having an insulating property remains in performing an electroforming method in an electroforming step. Accordingly, the wall part is covered by the insulating layer 34 with the resist layer 33 that remains. Thus, the wall part is securely insulated by cooperation of the insulating layer 34 and the resist layer 33 that remains. In this aspect also, the metal grating structure DG manufacturing method according to the embodiment is advantageous in finely forming the metal parts of a grating structure by an electroforming method in an electroforming step.

Figure 13:
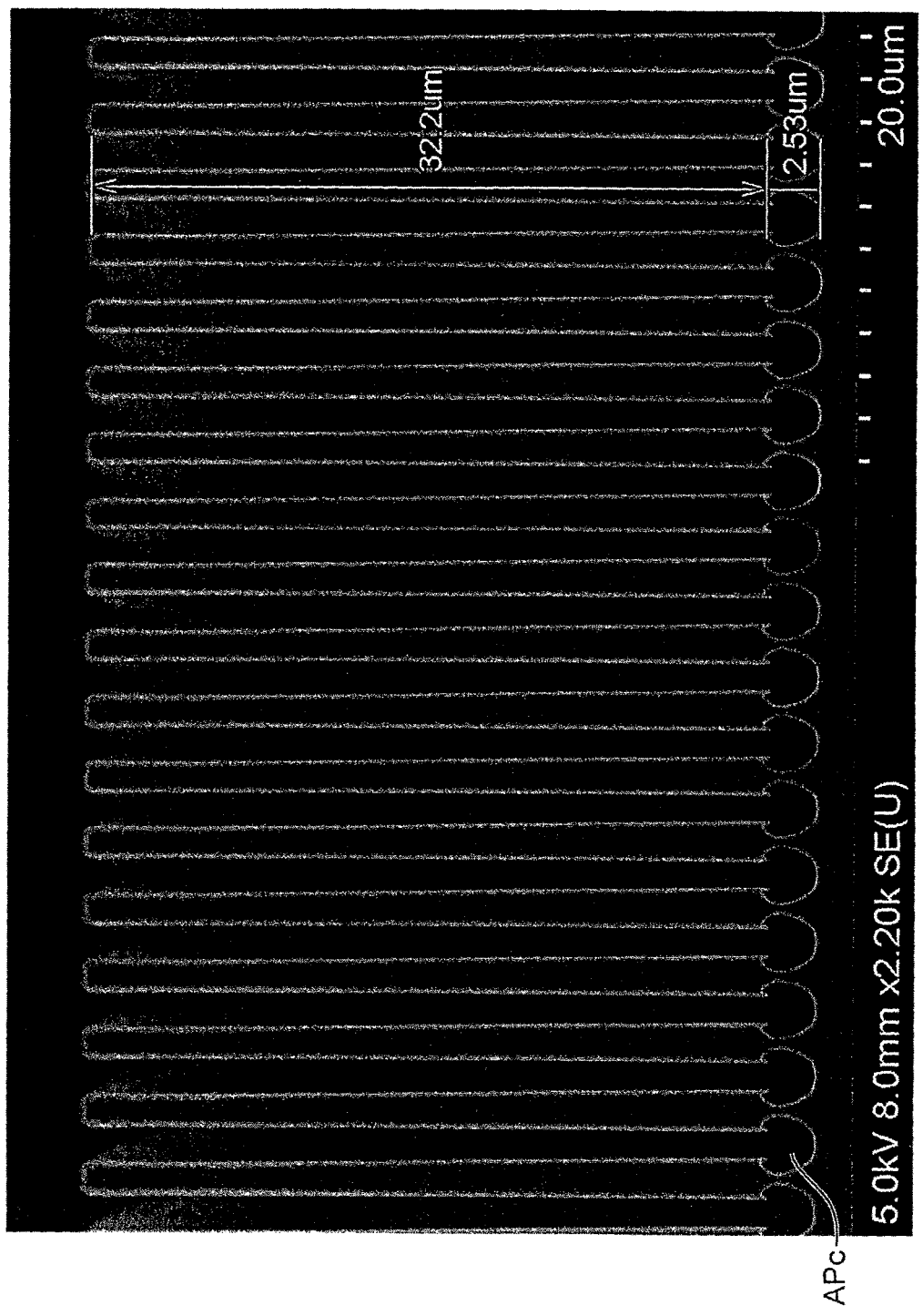
FIG. 13 is a diagram showing another shape of bottom parts of concave parts.

FIG. 13 is a diagram showing another configuration of the bottom part of the concave part. In the first and second manufacturing methods, the deposition start tip concave part AP is the deposition start tip concave part APb whose both side surfaces (both side walls) are substantially vertical, and preferably, the deposition start tip concave part APa whose both side surfaces (both side walls) have a tapered shape. Alternatively, as shown in FIG. 13, the deposition start tip concave part AP may be a deposition start tip concave part APc whose side surface has a curved surface shape. The deposition start tip concave part APc shown in FIG. 13 is such that both side surfaces thereof have an outwardly convex spherical shape, and a cross section thereof has a shape like a cross section of an apple. In the example shown in FIG. 13, the depth of a slit groove SD formed by the etching step is 32.2 μm, and the depth of a deposition start tip concave part APc formed by the removing/surface area increasing step is 2.53 μm.

The deposition start tip concave part APc having the above shape can be formed by performing ICP dry etching with use of gas suitable for etching a silicon substrate, for instance, $SF_6$ gas in the surface area increasing step. Further, for instance, the deposition start tip concave part APc can be formed by performing isotropic wet etching with use of a mixed solution containing nitric acid and hydrofluoric acid in the surface area increasing step. Forming the deposition start tip concave part APc having the above shape also increases the surface area of the silicon substrate 30 to be exposed. As a result, the electrically conductive surface area in the electroforming step increases. This is advantageous in suppressing a variation of metal deposition speed in each of the slit grooves SD. Thus, the second metal grating structure DG manufacturing method according to the embodiment is advantageous in manufacturing a metal grating structure DG having a substantially uniform deposition length of a metal part in each of the slit grooves SD by an electroforming method.

Further, in the first and second manufacturing methods, a diffraction grating DG has a one-dimensional periodic structure. The embodiment is not limited to the above. A diffraction grating DG may be a diffraction grating having a two-dimensional periodic structure. For instance, the diffraction grating DG of a two-dimensional periodic structure is configured such that grating dots serving as diffraction members are equidistantly arranged away from each other at a predetermined interval in linearly independent two directions. The diffraction grating of a two-dimensional periodic structure having the above configuration can be formed by forming holes of a high aspect ratio in a flat surface at a two-dimensional period, and filling the holes with metal as with the above configuration; or by forming upright columns of a high aspect ratio on a flat surface at a two-dimensional period, and filling a space around the columns with metal as with the above configuration.

(Talbot Interferometer and Talbot-Lau Interferometer)

The metal grating structure DG according to the embodiment is capable of forming metal parts with a high aspect ratio. Accordingly, the metal grating structure DG can be appropriately used in an X-ray Talbot interferometer and an X-ray Talbot-Lau interferometer. In the following, an X-ray Talbot interferometer and an X-ray Talbot-Lau interferometer incorporated with the metal grating structure DG are described.

Figure 14:
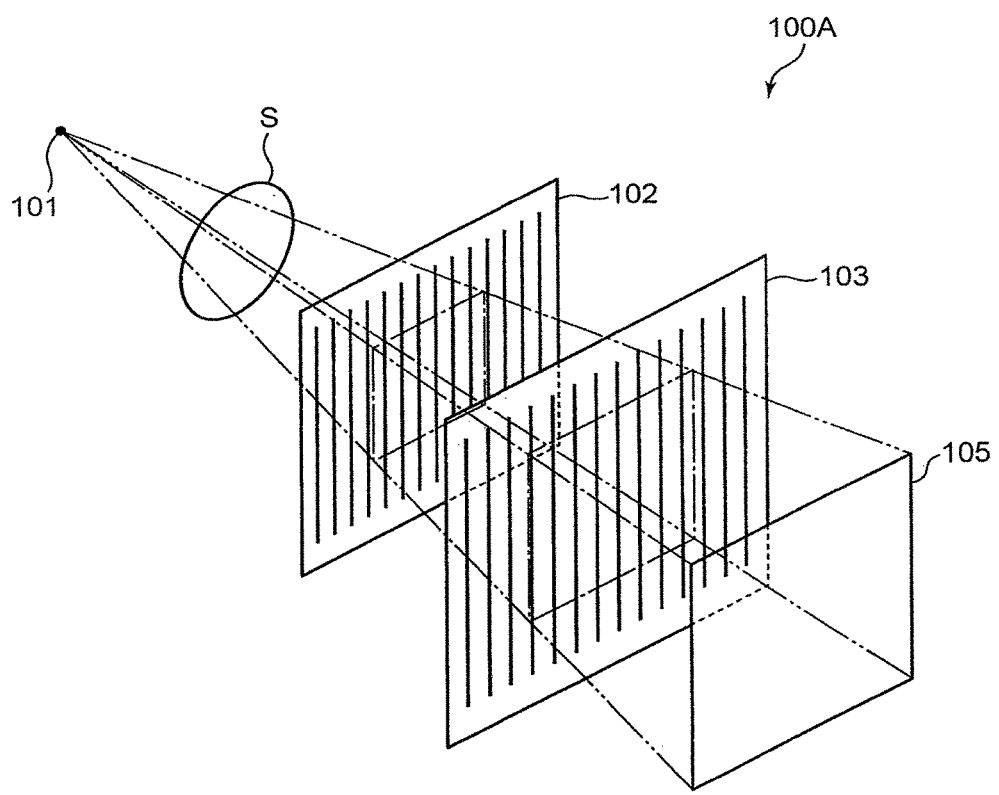
FIG. 14 is a perspective view showing a configuration of an X-ray Talbot interferometer according to an embodiment.
Figure 15:
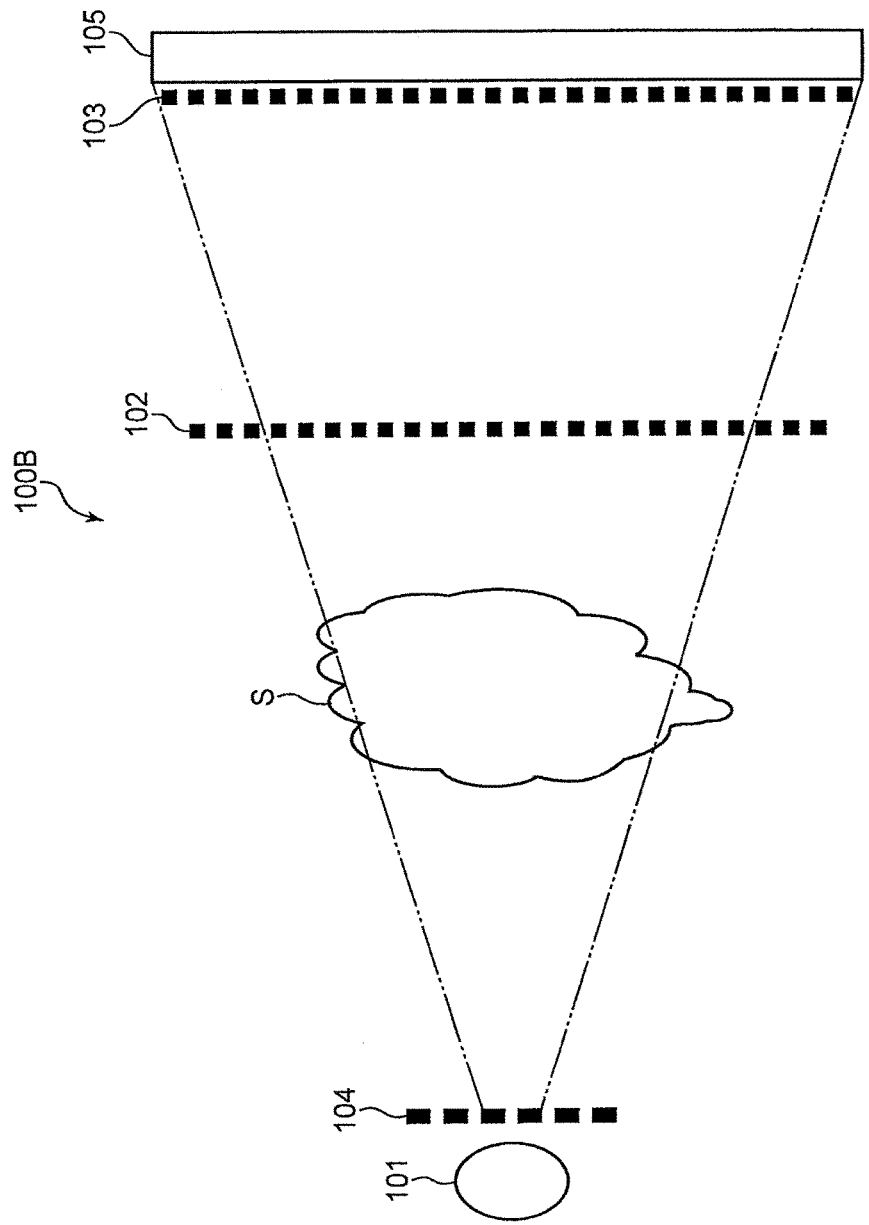
FIG. 15 is a top plan view showing a configuration of an X-ray Talbot-Lau interferometer according to an embodiment.

FIG. 14 is a perspective view showing a configuration of an X-ray Talbot interferometer according to an embodiment. FIG. 15 is a top plan view showing a configuration of an X-ray Talbot-Lau interferometer according to an embodiment.

As shown in FIG. 14, an X-ray Talbot interferometer 100A according to the embodiment is provided with an X-ray source 101 which outputs X-ray of a predetermined wavelength, a first diffraction grating 102 of phase-type which diffracts the X-ray output from the X-ray source 101, and a second diffraction grating 103 of amplitude-type which forms an image contrast by diffracting the X-ray diffracted by the first diffraction grating 102. The first and second diffraction gratings 102 and 103 are configured to satisfy the conditions that define an X-ray Talbot interferometer. An X-ray image having an image contrast to be generated by the second diffraction grating 103 is detected by an X-ray image detector 105 which detects X-ray, for instance. In the X-ray Talbot interferometer 100A, at least one of the first diffraction grating 102 and the second diffraction grating 103 has the aforementioned metal grating structure DG.

The conditions for defining the Talbot interferometer 100A are expressed by the following formulas 1 and 2. The formula 2 is made based on the premise that the first diffraction grating 102 is a phase-type diffraction grating.

$$I=\lambda/(a/(L+Z1+Z2)) \qquad \text{formula (1)}$$

$$Z1=(m+\tfrac{1}{2})\times(d^2/\lambda) \qquad \text{formula (2)}$$

where I denotes a coherence length, λ denotes a wavelength of X-ray (ordinarily, a center wavelength), a denotes an aperture diameter of the X-ray source 101 in a direction substantially orthogonal to a diffraction member of a diffraction grating, L denotes a distance from the X-ray source 101 to the first diffraction grating 102, Z1 denotes a distance from the first diffraction grating 102 to the second diffraction grating 103, Z2 denotes a distance from the second diffraction grating 103 to the X-ray image detector 105, m denotes an integer, and d denotes a period of a diffraction member (a period of a diffraction grating, a grating constant, a distance between centers of diffraction members adjacent to each other, or the pitch P).

In the X-ray Talbot interferometer 100A having the above configuration, X-ray is output from the X-ray source 101 toward the first diffraction grating 102. The output X-ray generates a Talbot effect on the first diffraction grating 102, and forms a Talbot image. The Talbot image forms an image contrast having moire fringes while passing through the second grating 103. Then, the image contrast is detected by the X-ray image detector 105.

The Talbot effect is such that an image (a self image of the diffraction grating) identical to an image of the diffraction grating is formed at a position away from the diffraction grating by a certain distance by incidence of light onto the diffraction grating. The certain distance is called a Talbot distance L, and the self image is called a Talbot image. The Talbot distance L is Z1 (L=Z1) as expressed by the formula 2, in the case where the diffraction grating is a phase-type diffraction grating. The Talbot image is such that a mirror image is generated when the Talbot distance is equal to an odd multiple of L (=(2m+1) where L, m is an integer), and a normal image is generated when the Talbot distance is equal to an even multiple of L (=2 mL).

In the case where a subject S is disposed between the X-ray source 101 and the first diffraction grating 102, the moire fringes are modulated by the subject S. The modulation amount is proportional to an angle at which X-ray is bent by refraction effect by the subject S. Accordingly, it is possible to detect the subject S and the inner structure of the subject S by analyzing the moire fringes.

In the Talbot interferometer 100A having the configuration as shown in FIG. 14, the X-ray source 101 is a single spot light source. Such a single spot light source can be configured by additionally providing a single slit plate having a single slit formed therein. X-ray output from the X-ray source 101 passes through the single slit formed in the single slit plate, and is irradiated toward the first diffraction grating 102 via the subject S. The slit is an oblong rectangular opening extending in one direction.

On the other hand, as shown in FIG. 15, a Talbot-Lau interferometer 100B is provided with an X-ray source 101, a multi-slit plate 104, a first diffraction grating 102, and a second diffraction grating 103. Specifically, the Talbot-Lau interferometer 100B is provided with, in addition to the Talbot interferometer 100A shown in FIG. 14, the multi-slit plate 104 having an array of slits formed therein on the X-ray output side of the X-ray source 101.

The multi-slit plate 104 may have a grating structure manufactured by the metal grating structure DG manufacturing method according to the embodiment. Manufacturing the multi-slit plate 104 by the metal grating structure DG manufacturing method according to the embodiment makes it possible to transmit X-ray through the slits (the second silicon parts 12a), and to securely block transmittance of X-ray by the metal parts 12b. Accordingly, it is possible to clearly discriminate between X-ray transmittance and non-transmittance. Thus, the multi-slit plate 104 can securely use X-ray output from the X-ray source 101, as a multi-light source.

As compared with the Talbot interferometer 100A, configuring the Talbot-Lau interferometer 100B increases the amount of X-ray to be irradiated to the first diffraction grating 102 via the subject S. This is more advantageous in obtaining moire fringes in a satisfactory manner.

Some examples of the first diffraction grating 102, the second diffraction grating 103, and the multi-silt plate 104 to be used in the Talbot interferometer 100A or in the Talbot-Lau interferometer 100B are described as follows. It should be noted that in the examples, the first silicon parts 12a and the metal parts 12b are each formed to have a same width, and the metal parts 12b are made of gold.

As an example, in the case where the distance R1 from the X-ray source 101 or from the multi-slit plate 104 to the first diffraction grating 102 is 2 m, and the distance R2 from the X-ray source 101 or from the multi-slit plate 104 to the second diffraction grating 103 is 2.5 m, the pitch P of the first diffraction grating 102 is 5 μm, and the thickness of the metal part 12b thereof is 3 μm; the pitch P of the second diffraction grating 103 is 6 μm, and the thickness of the metal part 12b thereof is 100 μm (an aspect ratio=100/3); and the pitch P of the multi-slit plate 104 is 30 μm, and the thickness of the metal part 12b thereof is 100 μm.

As another example, in the case where the distance R1 from the X-ray source 101 or from the multi-slit plate 104 to the first diffraction grating 102 is 1.8 m, and the distance R2 from the X-ray source 101 or from the multi-slit plate 104 to the second diffraction grating 103 is 2.5 m, the pitch P of the first diffraction grating 102 is 7 μm, and the thickness of the metal part 12b thereof is 3 μm; the pitch P of the second diffraction grating 103 is 10 μm, and the thickness of the metal part 12b thereof is 100 μm (an aspect ratio=100/5); and the pitch P of the multi-slit plate 104 is 20 μm, and the thickness of the metal part 12b thereof is 100 μm.

(X-Ray Imaging Device)

The metal grating structure DG can be utilized in a variety of optical devices. The metal parts 12b can be formed with a high aspect ratio. Accordingly, for instance, the metal grating structure DG can be appropriately used in an X-ray imaging device. In particular, an X-ray imaging device incorporated with an X-ray Talbot interferometer employs one of the phase contrast methods for obtaining a transmitted image of a subject by handling X-ray as a wave, and by detecting a phase shift in X-ray resulting from transmittance through the subject. The X-ray imaging device has the advantages that sensitivity improvement as high as about 1,000 times of an absorption contrast method for obtaining an image, in which differences in magnitudes of X-ray absorption by a subject are used as contrast, can be expected and that the amount of X-ray radiation can be reduced to one-hundredth or to one-thousandth, for instance. In this embodiment, an X-ray imaging device provided with an X-ray Talbot interferometer incorporated with the aforementioned diffraction grating DG is described.

Figure 16:
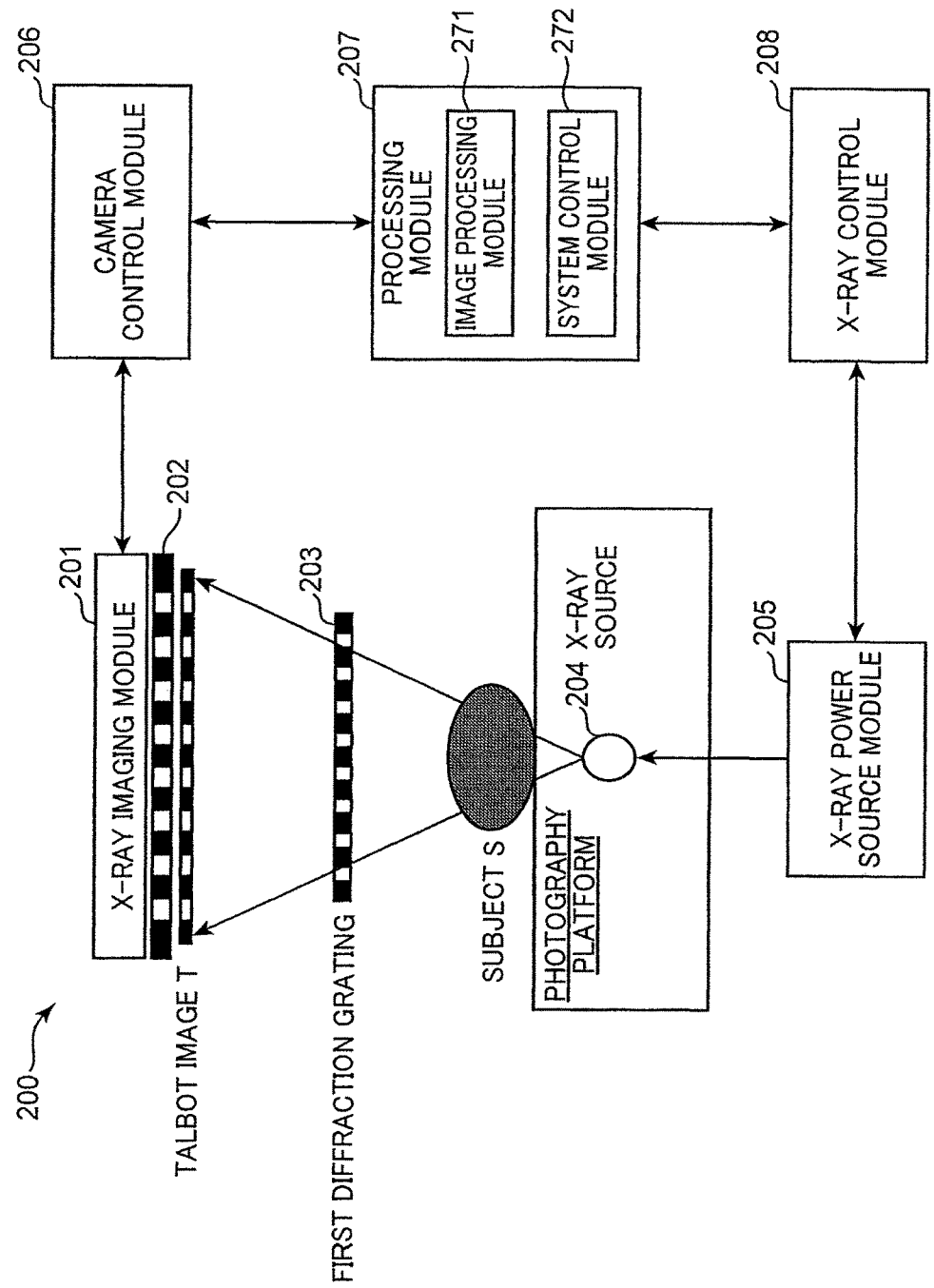
FIG. 16 is an explanatory diagram showing a configuration of an X-ray imaging device according to an embodiment.

FIG. 16 is an explanatory diagram showing a configuration of an X-ray imaging device according to an embodiment. Referring to FIG. 16, an X-ray imaging device 200 is provided with an X-ray imaging module 201, a second diffraction grating 202, a first diffraction grating 203, and an X-ray source 204. The X-ray imaging device 200 according to the embodiment is further provided with an X-ray power source module 205 which supplies electric power to the X-ray source 204, a camera control module 206 which controls an imaging operation of the X-ray imaging module 201, a processing module 207 which controls the overall operation of the X-ray imaging device 200, and an X-ray control module 208 which controls X-ray radiation by the X-ray source 204 by controlling power supply of the X-ray power source module 205.

The X-ray source 204 is a device that outputs X-ray by receiving electric power from the X-ray power source module 205 to irradiate the X-ray to the first diffraction grating 203. The X-ray source 204 is, for instance, a device that outputs X-ray by application of a high voltage supplied from the X-ray power source module 205 between a cathode and an anode of the X-ray source 204, and by collision of electrons discharged from filaments of the cathode with the anode.

The first diffraction grating 203 is a transmissive diffraction grating that generates a Talbot effect by X-ray output from the X-ray source 204. For instance, the first diffraction grating 203 is a diffraction grating manufactured by the metal grating structure DG manufacturing method according to the embodiment. The first diffraction grating 203 is configured to satisfy the conditions that generate a Talbot effect. The first diffraction grating 203 is a phase-type diffraction grating having a grating interval sufficiently larger than the wavelength of X-ray output from the X-ray source 204, for instance, having a grating constant (a period of a diffraction grating) d of about twenty times or more of the wavelength of X-ray. The first diffraction grating 203 may be an amplitude-type diffraction grating substantially equivalent to the above.

The second diffraction grating 202 is a transmissive amplitude-type diffraction grating which is disposed at a position away from the first diffraction grating 203 substantially by a Talbot distance L, and which diffracts X-ray diffracted by the first diffraction grating 203. As with the case of the first diffraction grating 203, the second diffraction grating 202 is also a diffraction grating manufactured by the metal grating structure DG manufacturing method according to the embodiment.

The first and second diffraction gratings 203 and 202 are configured to satisfy the conditions that define a Talbot interferometer expressed by the aforementioned formulas 1 and 2.

The X-ray imaging module 201 is a device for imaging an image of X-ray diffracted by the second diffraction grating 202. For instance, the X-ray imaging module 201 is a flat panel detector (FPD) provided with a two-dimensional image sensor configured such that a film layer including a scintillator for absorbing X-ray energy and emitting fluorescence is formed on a light receiving surface; or an image intensifier camera provided with an image intensifier module which converts incident photons into electrons on a photoelectric surface, multiplies the electrons by a micro-channel plate, and causes the multiplied electron groups to collide with fluorescent bodies to emit fluorescence, and a two-dimensional image sensor which captures an image of light output from the image intensifier module.

The processing module 207 is a device for controlling the overall operation of the X-ray imaging device 200 by controlling the respective parts of the X-ray imaging device 200. For instance, the processing module 207 is constituted of a microprocessor and peripheral circuits thereof, and is functionally provided with an image processing module 271 and a system control module 272.

The system control module 272 controls the X-ray source 204 to perform X-ray radiation via the X-ray power source module 205 by sending/receiving a control signal to/from the X-ray control module 208, and controls the X-ray imaging module 201 to perform an imaging operation by sending/receiving a control signal to/from the camera control module 206. X-ray is irradiated toward the subject S under the control of the system control module 272, an image generated by the X-ray radiation is captured by the X-ray imaging module 201, and an image signal is input to the processing module 207 via the camera control module 206.

The image processing module 271 processes an image signal generated by the X-ray imaging module 201, and generates an image of the subject S.

In the following, an operation to be performed by the X-ray imaging device according to this embodiment is described. A subject S is disposed between the X-ray source 204 and the first diffraction grating 203 by letting the subject S lie on a photography platform equipped with the X-ray source 204 therein (or on the back surface thereof), for instance. When imaging of the subject S is instructed by an unillustrated operating module by a user (an operator) operating the X-ray imaging device 200, the system control module 272 in the processing module 207 outputs a control signal to the X-ray control module 208 for irradiating X-ray to the subject S. By the control signal, the X-ray control module 208 causes the X-ray power source module 205 to supply electric power to the X-ray source 204, and the X-ray source 204 outputs X-ray to irradiate the X-ray to the subject S.

The irradiated X-ray passes through the first diffraction grating 203 via the subject S, and is diffracted by the first diffraction grating 203, whereby a Talbot image T as a self image of the first diffraction grating 203 is formed at a position away from the first diffraction grating 203 by a Talbot distance L (=Z1).

The thus-formed Talbot image T of X-ray is diffracted by the second diffraction grating 202, and an image constituted of moire fringes is formed by generation of moire. The image constituted of moire fringes is captured by the X-ray imaging module 201 whose exposure time is controlled by the system control module 272, for instance.

The X-ray imaging module 201 outputs an image signal indicative of an image of moire fringes to the processing module 207 via the camera control module 206. The image signal is processed by the image processing module 271 in the processing module 207.

The subject S is disposed between the X-ray source 204 and the first diffraction grating 203. Accordingly, the phase of the X-ray that passes through the subject S is shifted from the phase of the X-ray that does not pass through the subject S. As a result, the X-ray incident to the first diffraction grating 203 includes distortion on a wave front thereof, and the Talbot image T is deformed according to the distortion. The moire fringes of the image generated by overlapping the Talbot image T and the second diffraction grating 202 are modulated by the subject S. The modulation amount is proportional to an angle at which the X-ray is bent by refraction effect by the subject S. Accordingly, it is possible to detect the subject S and the inner structure of the subject S by analyzing the moire fringes. Further, it is possible to form a tomographic image of the subject S by X-ray computed tomography (CT) by imaging the subject S from different angles.

The second diffraction grating 202 in this embodiment has the metal grating structure DG provided with the metal parts 12b of a high aspect ratio according to the embodiment. Accordingly, it is possible to obtain moire fringes in a satisfactory manner, thereby obtaining an image of the subject S with high precision.

Further, in the metal grating structure DG, the plate like parts 32 (the second silicon parts 12a) of the silicon substrate 30 are dry etched by a Bosch process. This makes it possible to make the side surfaces of the slit grooves SD flat, thereby forming the second diffraction grating 202 with high precision. This is advantageous in obtaining moire fringes in a satisfactory manner, thereby obtaining an image of the subject S with high precision.

The aforementioned X-ray imaging device 200 is such that a Talbot interferometer is constituted of the X-ray source 204, the first diffraction grating 203, and the second diffraction grating 202. Alternatively, a Talbot-Lau interferometer may be configured by additionally disposing the metal grating structure DG according to the embodiment as a multi-slit member on the X-ray output side of the X-ray source 204. Configuring such a Talbot-Lau interferometer makes it possible to increase the amount of X-ray to be irradiated to the subject S, as compared with a configuration of disposing a single slit member. This is advantageous in obtaining moire fringes in a satisfactory manner, thereby obtaining an image of the subject S with high precision.

Further, in the aforementioned X-ray imaging device 200, a subject S is disposed between the X-ray source 204 and the first diffraction grating 203. Alternatively, a subject S may be disposed between the first diffraction grating 203 and the second diffraction grating 202.

Further, in the aforementioned X-ray imaging device 200, an image of X-ray is captured by the X-ray imaging module 201, and electronic data of the image is obtained. Alternatively, an image of X-ray may be obtained by an X-ray film.

The specification discloses the aforementioned features. The following is a summary of the primary features of the embodiment.

A method for manufacturing a metal grating structure according to an aspect includes a resist layer forming step of forming a resist layer on a principal plane of a silicon substrate; a patterning step of patterning the resist layer, and removing the patterned portion of the resist layer; an etching step of etching the silicon substrate corresponding to the removed portion of the resist layer by a dry etching method, and forming a concave part of a predetermined depth; an insulating layer forming step of forming an insulating layer on an inner surface of the concave part in the silicon substrate; a removing/surface area increasing step of removing a portion of the insulating layer formed on a bottom part of the concave part, and etching the silicon substrate at the bottom part of the concave part to increase a surface area of the bottom part of the concave part as compared with a state before the etching; and an electroforming step of applying a voltage to the silicon substrate to fill the concave part with metal by an electroforming method.

According to the metal grating structure manufacturing method having the above configuration, a silicon substrate is dry etched. Accordingly, for instance, it is possible to form a concave part of a high ratio (an aspect ratio of the concave part=depth/width) of depth to width of the concave part such as a slit groove or a columnar hole. As a result, in the metal grating structure manufacturing method having the above configuration, it is possible to manufacture a metal grating structure having a metal part of a high aspect ratio by filling the concave part with metal. In filling the concave part with metal by an electroforming method in the electroforming step, first of all, in the insulating layer forming step, an insulating layer is formed on the inner surface of the concave part, and then, in the removing/surface area increasing step, the bottom part of the concave part in the insulating layer is removed, and a portion of the silicon substrate exposed from the bottom part of the concave part is etched to increase the surface area of the bottom part of the concave part. Accordingly, in the insulating layer forming step, it is possible to form a silicon oxide film (an $SiO_2$ film) of a predetermined film thickness, and to insulate, by the insulating layer, a wall surface portion (inner side surface portions of the concave part) of a wall part of the silicon substrate that constitutes the concave part and remains in the etching step, while making the bottom part of the concave part electrically conductive. Accordingly, the metal is securely precipitated and deposited on the bottom part of the concave part, without precipitating and depositing the metal on the wall surface (inner side surfaces) of the concave part. Thus, the metal grating structure manufacturing method having the above configuration can effectively prevent formation of voids, because the metal is preferentially deposited on the bottom part of the concave part. Accordingly, the metal grating structure manufacturing method having the above configuration is advantageous in finely forming the metal part of a grating structure by an electroforming method. Further, in the removing/surface area increasing step, in addition to removing the insulating layer formed on the bottom part of the concave part, a portion of the silicon substrate exposed from the bottom part of the concave part is etched to increase the surface area of the bottom part of the concave part, as compared with a state before the etching. In the above configuration, the surface area of the silicon substrate to be exposed increases. As a result, the electrically conductive surface area in the electroforming step increases. This is advantageous in suppressing a variation of metal deposition speed in each of the concave parts. Thus, the metal grating structure manufacturing method having the above configuration is advantageous in manufacturing a metal grating structure having a substantially uniform deposition length of a metal part in each of the concave parts by an electroforming method.

Further, in the metal grating structure manufacturing method having the above configuration, in the removing/surface area increasing step, the surface area of the bottom part of the concave part may be increased as compared with the state before the etching by removing the portion of the insulating layer formed on the bottom part of the concave part, and by etching the silicon substrate at the bottom part of the concave part to such an extent that a side surface of the concave part has a tapered shape and a depth of the concave part is deeper than the predetermined depth.

According to the metal grating structure manufacturing method having the above configuration, it is possible to increase the electrically conductive surface area in the electroforming step by forming a portion of the silicon substrate to be exposed into a tapered shape. This is advantageous in preventing formation of voids in depositing metal in the electroforming step.

Further, in the metal grating structure manufacturing method having the above configuration, in the removing/surface area increasing step, the surface area of the bottom part of the concave part may be increased as compared with the state before the etching by removing the portion of the insulating layer formed on the bottom part of the concave part, and by etching the silicon substrate at the bottom part of the concave part to such an extent that a side surface of the concave part has a curved surface shape and a depth of the concave part is deeper than the predetermined depth.

According to the metal grating structure manufacturing method having the above configuration, it is possible to form a portion of the silicon substrate to be exposed into a curved surface shape. This is advantageous in increasing the surface area, as compared with a configuration, in which the concave part is etched substantially vertically.

Further, in the metal grating structure manufacturing method having one of the above configurations, in the insulating layer forming step, an insulating layer may be formed on an inner surface of the concave part in the silicon substrate by one of a deposition method, a thermal oxidation method, and an anodic oxidation method.

According to the metal grating structure manufacturing method having the above configuration, in the case where a deposition method such as a chemical vapor deposition method, a sputtering method, or a vapor deposition method is used, the deposition method is advantageous in forming an insulating layer having enhanced fineness, and also makes it relatively easy to control the film thickness. In the case where a thermal oxidation method is used, the thermal oxidation method is advantageous in forming a silicon oxide film having enhanced fineness and adhesiveness, and also makes it relatively easy to control the film thickness. In the case where an anodic oxidation method is used, the anodic oxidation method is advantageous in forming a silicon oxide film having enhanced fineness, adhesiveness, and uniformity in film thickness, and also makes it relatively easy to control the film thickness. Accordingly, the metal grating structure manufacturing method having the above configuration is advantageous in forming a fine insulating layer of a predetermined film thickness capable of securing electrical insulation in an electroforming method in the electroforming step.

Further, in the metal grating structure manufacturing method having one of the above configurations, the dry etching method may be RIE (reactive ion etching).

According to the metal grating structure manufacturing method having the above configuration, it is possible to perform anisotropic etching by RIE. Accordingly, it is possible to etch the silicon substrate in a depth direction (a direction perpendicular to the principal plane (a surface)). This makes it relatively easy to form the concave part.

Further, in the metal grating structure manufacturing method having one of the above configurations, the dry etching method may be a Bosch process.

According to the metal grating structure manufacturing method having the above configuration, it is possible to dry etch the silicon substrate by the Bosch process. Accordingly, this is advantageous in making a side surface of the concave part flat, and in forming a metal grating structure with high precision.

Further, in the metal grating structure manufacturing method having one of the above configurations, the silicon substrate may be an n-type silicon substrate.

According to the metal grating structure manufacturing method having the above configuration, the electric conductive type of the silicon substrate is n-type. Accordingly, in the case where the silicon substrate is used as a cathode in an electroforming method, it is easy to donate electrons from the silicon substrate to a plating solution. This is advantageous in precipitating metal.

Further, the metal grating structure manufacturing method having one of the above configurations is used in manufacturing a metal grating structure for use in an X-ray Talbot interferometer or an X-ray Talbot-Lau interferometer.

As described above, X-ray radiation requires a high aspect ratio. Use of the metal grating structure manufacturing method having one of the above configurations makes it possible to manufacture a diffraction grating or a metal grating structure provided with a multi-slit plate for use in an X-ray Talbot interferometer or an X-ray Talbot-Lau interferometer provided with a finely formed metal part having a uniform deposition length and a high aspect ratio.

A metal grating structure according to another aspect is manufactured by the metal grating structure manufacturing method having one of the above configurations.

The metal grating structure to be manufactured by the metal grating structure manufacturing method having one of the above configurations is provided with a finely formed metal part having a uniform deposition length and a high aspect ratio. Accordingly, the metal grating structure having the above configuration can be appropriately used for X-ray devices, and can be more advantageously used particularly for an X-ray Talbot interferometer or an X-ray Talbot-Lau interferometer.

Further, an X-ray imaging device according to yet another aspect includes an X-ray source which outputs an X-ray; a Talbot interferometer or a Talbot-Lau interferometer on which the X-ray output from the X-ray source is irradiated; and an X-ray imaging element which captures an image of X-ray by the Talbot interferometer or the Talbot-Lau interferometer, wherein the Talbot interferometer or the Talbot-Lau interferometer includes the metal grating structure having the above configuration.

The X-ray imaging device having the above configuration is incorporated with, as a metal grating structure constituting a Talbot interferometer or a Talbot-Lau interferometer, the aforementioned metal grating structure provided with a finely formed metal part having a uniform deposition length. This is advantageous in securely diffracting an X-ray, thereby obtaining a clear image of the X-ray.

Further, an intermediate product for a metal grating structure according to still another aspect is an intermediate product for a metal grating structure provided with a silicon substrate in which a plurality of concave parts are formed according to a predetermined pattern. Each of the concave parts has an insulating layer formed on an inner surface of the concave part from an opening end of the concave part to a predetermined depth in a depth direction of the concave part, and the silicon substrate is exposed from the inner surface in a region from a position corresponding to the predetermined depth to a deepest end of the concave part.

With use of the intermediate product for a metal grating structure, it is possible to manufacture a metal grating structure provided with a finely formed metal part having a substantially uniform deposition length and a high aspect ratio by filling the concave part with metal by an electroforming method.

This application is based on Japanese Patent Application No. 2011-164015 filed on Jul. 27, 2011, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

INDUSTRIAL APPLICABILITY

According to the present invention, it is possible to provide a metal grating structure for X-ray.

The invention claimed is:

1. A metal grating structure for X-ray, comprising:
a first silicon part having a plate form or a layer form; and
a grating portion, wherein
the grating portion includes a plurality of second silicon parts formed on the first silicon part, and a plurality of metal parts interposed between respective adjacent second silicon parts, each of the plurality of metal parts having a deposition start tip part extending into the first silicon part, and
each metal part is longer than each of the second silicon parts by a length of the deposition start tip part in a depth direction perpendicular to the first silicon part.

2. The metal grating structure for X-ray according to claim 1, wherein the deposition start tip part includes a concave part having side surfaces, one of the side surfaces having a tapered shape.

3. The metal grating structure for X-ray according to claim 2, wherein each of the side surfaces of the concave part have a tapered shape, and intersect with each other.

4. The metal grating structure for X-ray according to claim 1, wherein a ratio between a first depth of each of the second silicon parts and a second depth of the deposition start tip part is set to be from 99:1 to 80:20.

5. The metal grating structure for X-ray according to claim 1, wherein the deposition start tip part includes a concave part having side surfaces, one of the side surfaces having a curved shape.

6. The metal grating structure for X-ray according to claim 1, wherein the deposition start tip part includes a concave part which has side surfaces, each side surface having an outwardly convex spherical shape.

7. The metal grating structure for X-ray according to claim 1, wherein each of the metal parts has an aspect ratio of 5 or more.

8. The metal grating structure for X-ray according to claim 1, wherein the metal parts are made of metal selected from any one of gold, platinum, rhodium, ruthenium, iridium, indium, and nickel.

9. The metal grating structure for X-ray according to claim 1, wherein the first silicon part and the second silicon part are made of n-type silicon.

10. The metal grating structure for X-ray according to claim 1, further comprising:
   a first insulating layer between the surfaces of the second silicon parts and the metal parts.

11. The metal grating structure for X-ray according to claim 1, further comprising:
   a second insulating layer formed on an upper surface of each of the second silicon parts.

12. The metal grating structure for X-ray according to claim 1, wherein the first silicon part has a mirror-finished side surface opposite to a side surface in contact with the second silicon parts.

* * * * *